US012710405B1

(12) United States Patent
Liu et al.

(10) Patent No.: US 12,710,405 B1
(45) Date of Patent: Aug. 18, 2026

(54) KIT FOR DETECTING DRUG IN SAMPLE AND DETECTION METHOD THEREOF

(71) Applicant: Calibra Scientific, Inc., Hangzhou (CN)

(72) Inventors: Pengyun Liu, Hangzhou (CN); Yikun Li, Hangzhou (CN); Wenlie Huang, Hangzhou (CN); Shishan Fu, Hangzhou (CN); Weijia Wu, Hangzhou (CN); Huafen Liu, Hangzhou (CN)

(73) Assignee: Calibra Scientific, Inc., Hangzhou (CN)

( * ) Notice: Subject to any disclaimer, the term of this patent is extended or adjusted under 35 U.S.C. 154(b) by 0 days.

(21) Appl. No.: 19/272,396

(22) Filed: Jul. 17, 2025

(30) Foreign Application Priority Data

May 8, 2025 (CN) ........................ 202510589583.4

(51) Int. Cl.

| | |
|---|---|
| ***G01N 30/72*** | (2006.01) |
| ***B01D 15/38*** | (2006.01) |
| ***B01D 15/42*** | (2006.01) |
| ***B01J 20/10*** | (2006.01) |
| ***B01J 20/28*** | (2006.01) |
| ***B01J 20/292*** | (2006.01) |
| ***B03C 1/30*** | (2006.01) |
| ***G01N 30/14*** | (2006.01) |
| ***G01N 33/15*** | (2006.01) |
| *G01N 30/02* | (2006.01) |

(52) U.S. Cl.
CPC ..... *G01N 30/7233* (2013.01); *B01D 15/3885* (2013.01); *B01D 15/424* (2013.01); *B01J 20/103* (2013.01); *B01J 20/28009* (2013.01); *B01J 20/292* (2013.01); *B03C 1/30* (2013.01); *G01N 30/14* (2013.01); *G01N 33/15* (2013.01); *B03C 2201/18* (2013.01); *G01N 2030/027* (2013.01)

(58) Field of Classification Search
CPC .... G01N 30/7233; G01N 30/14; G01N 33/15; G01N 2030/027; B01D 15/3885; B01D 15/424; B01J 20/103; B01J 20/28009; B01J 20/292; B03C 1/30; B03C 2201/18
USPC .......................................................... 436/161
See application file for complete search history.

(56) References Cited

U.S. PATENT DOCUMENTS

| | | | | |
|---|---|---|---|---|
| 10,434,492 | B2 * | 10/2019 | Lu | B01J 20/3244 |
| 2017/0138940 | A1 * | 5/2017 | Goethel | B01D 15/02 |
| 2019/0015815 | A1 * | 1/2019 | Lawrence | B01J 20/283 |

* cited by examiner

*Primary Examiner* — Christine T Mui
(74) *Attorney, Agent, or Firm* — MUNCY, GEISSLER, OLDS & LOWE, P.C.

(57) ABSTRACT

The present application provides a kit for therapeutic drug monitoring, and a method and system thereof. A magnetic bead extraction method combined with LC-MS/MS detection is applied to drug concentration monitoring in human blood. A mixed magnetic bead solution containing a phospholipid depletion magnetic bead and a to-be-detected drug-adsorption magnetic bead is used for adsorption and extraction pretreatment of a drug to be detected in a sample. In conjunction with automated treatment equipment, the pretreatment efficiency is high such that the content of phospholipids in a supernatant is low, thereby greatly reducing the matrix effect and the chromatographic column flushing pressure. The method for therapeutic drug monitoring provided by the present application uses a unified pretreatment flow to achieve simultaneous extraction of multiple drugs. Moreover, by means of an automated magnetic bead extraction method, the steps for sample pretreatment can be completed rapidly, and the results for therapeutic drug monitoring can be obtained rapidly, such that the overall detection time is shortened, thereby providing a reliable laboratory examination basis for achieving individualized therapy.

4 Claims, 10 Drawing Sheets

KIT FOR DETECTING DRUG IN SAMPLE AND DETECTION METHOD THEREOF

CROSS-REFERENCE TO RELATED APPLICATIONS

The present application claims priority to Chinese Prior application No. 202510589583.4, filed on May 8, 2025, the claims, abstract, and representative drawing of which are incorporated as part of the present application.

BACKGROUND OF THE INVENTION

Field of the Invention

The present application relates to the technical field of medical diagnosis, and in particular, to a kit for therapeutic drug monitoring, and a method and system thereof.

Description of the Related Art

Therapeutic drug monitoring (TDM) is a technology that tailor-makes dosage regimens by analyzing drugs, biomarkers, and the like in different patient individuals, to achieve optimal efficacy and minimal adverse reactions so as to achieve individualized therapy.

In a case of nearly identical drug dosages, in-vivo steady-state drug concentrations of different individuals can vary by over 20-fold, which may cause different reactions, such as effective, ineffective, and toxic reactions. The main reason is the differences between drugs in absorption, distribution, metabolism, and excretion due to the differences between patients in comorbidities, age, drug combination, and genetic characteristics. Therefore, quantitatively measuring drug concentrations in plasma or serum for dosage titration of patient individuals to obtain optimal efficacy and better tolerance and reduce toxic risks is a necessary means to achieve individualized therapy.

Drugs requiring TDM generally fall into five categories: 1. Drugs with a low therapeutic index, a narrow safety margin, and a range of therapeutic concentrations very close to the range of toxic concentrations, such as cardiac glycosides and aminoglycoside antibiotics. 2. Drugs requiring long-term use without clear, observable therapeutic endpoints or indicators and timely, prone-to-observation, and efficacy-predictable clinical indicators to adjust dosages, such as antiepileptic drugs and immunosuppressants. 3. Drugs having a nonlinear pharmacokinetic feature. 4. Drugs with large pharmacokinetic individual differences, very potent pharmacological activity, and very large differences in drug metabolism individualization due to genetic factors and the like, such as tricyclic antidepressants. 5. Drugs for which therapeutic failure carries severe consequences, such as immunosuppressants and some antibiotics.

Current TDM mainly uses immunoassays and chromatographic methods. The immunoassays have the characteristics of short detection time, small sample quantity demanded, simple operation, and high degree of automation. However, the immunoassays are limited to the types of drugs of detection kits and the possibility of cross-reactivity with parent drug metabolites, require the development of corresponding kits for each drug, and are not suitable for new drug research. The chromatographic methods solve the shortcomings of the immunoassays, have the advantages such as rapid new method design, good flexibility, accurate quantification, good selectivity, high sensitivity, and high precision, and become the most widely used TDM analytical methods. For example, liquid chromatography-tandem mass spectrometry (LC-MS/MS) is a chromatographic method that is currently domestically and internationally recognized for better sensitivity, reproducibility, accuracy, and higher dynamic linear range, and can provide more reliable testing data for clinical diagnosis.

At present, in the use of LC-MS/MS for TDM, the most common pretreatment method is protein precipitation, i.e., mixing a sample with precipitating agents such as acids, metal salts, organic solvents in specific ratios, followed by uniform vortex mixing, centrifugation to collect a supernatant or diluting a supernatant for on-machine detection. The method has relatively significant matrix effects, which may affect the sensitivity and accuracy of detection results when chromatographic separation is incomplete; moreover, the drug concentrations are diluted, and some low-concentration drugs cannot meet the requirements for detection, requiring further nitrogen blowdown concentration and reconstitution or more complex pretreatment enrichment methods, such as solid-phase extraction. Meanwhile, automation is an important part of the development of detection technology. By means of an automation platform, the sample treatment efficiency and accuracy can be effectively improved, saving personnel costs, and achieving better project management.

Throughout the development of research on the TDM pretreatment technology, there have been a variety of phospholipid depletion plates available on the market for the removal of impurities. Waters' Ostro protein and phospholipid removal plates and Biotage's ISOLUTE® PLD+ protein and phospholipid removal plates can remove most of the proteins and phospholipids in plasma that cause an ion suppression effect, by using simple steps of solvent precipitation and filtration. Pretreatment operations generally include: first, adding a precipitating agent (e.g., acetonitrile with 1% formic acid), then adding a biological sample, and carrying out suction or shaking for thorough mixing; using a 96-well positive-pressure instrument for positive-pressure filtration, and collecting a filtrate for subsequent direct injection or concentration. The use of a phospholipid removal plate is simple in operation and good in protein and phospholipid removal effects. However, the phospholipid removal plate has a relatively high price and prolonged pretreatment time, is not suitable for different types of drugs and some types, and cannot be applied to domestic daily drug monitoring.

In terms of automation, Shimadzu launched a fully automated pretreatment system CLAM-2030 in recent years, which has been applied in drug monitoring and forensic screening. The system can conduct fully automated protein precipitation on a biological sample, eliminating human errors in a manual pretreatment process, improving result reproducibility and analytical efficiency, and improving the efficiency of a protein precipitation method; moreover, sample tubes and a negative-pressure suction filtration system are specially designed, which are expensive. However, the influence of matrix effects is still unresolved.

Thus, there is an urgent need for a sample pretreatment method that is simpler, can achieve full automation, and is compatible with various drug monitoring processes, thereby establishing a more efficient and convenient TDM system that is more accurate and reliable in monitoring results.

BRIEF SUMMARY OF THE INVENTION

For the problems in the prior art, the present application provides a kit for therapeutic drug monitoring, and a method and system thereof. A magnetic bead extraction method combined with LC-MS/MS detection is applied to concentration monitoring of therapeutic drugs. A mixed magnetic bead solution containing a phospholipid depletion magnetic bead and a to-be-detected drug-adsorption magnetic bead is used for one-time adsorption and phospholipid removal and extraction pretreatment of a drug to be detected in a sample. In conjunction with automated treatment equipment, the pretreatment efficiency is high such that the content of phospholipids in a supernatant is very low, thereby greatly reducing the matrix effect and the chromatographic column flushing pressure. The method for therapeutic drug monitoring provided by the present application uses a unified pretreatment flow to achieve simultaneous extraction of multiple drugs. Moreover, by means of an automated magnetic bead extraction method, the steps for sample pretreatment can be completed rapidly, and the results for monitoring plasma-drug concentrations of therapeutic drugs can be obtained rapidly, such that the overall detection time is shortened, thereby providing a reliable laboratory examination basis for achieving individualized therapy.

In an aspect, the present application provides a kit for therapeutic drug monitoring, including a phospholipid depletion magnetic bead solution, wherein the phospholipid depletion magnetic bead solution includes a magnetic bead for removing phospholipids in a sample.

The LC-MS/MS-based TDM analysis technology has been widely applied in drug monitoring, but still has technical bottlenecks in the sample pretreatment process. Currently, a protein precipitation method is mostly used for sample pretreatment and has the following problems: 1. the matrix effect is still present, and macromolecules such as phospholipids in samples are not effectively removed, affecting sample detection data and chromatographic column service life; 2. the samples are diluted in the pretreatment process, and the drugs with relatively low contents require nitrogen blowdown concentration, which is time-consuming and complicated; 3. The method involves multiple tools and multiple operations such as uniform vortex mixing and centrifugation, and it is difficult to achieve automation.

The magnetic bead-based automated sample pretreatment and LC-MS/MS analysis method provided in the present application uses the characteristic of magnetic particles to specifically bind to target molecules, target components can be efficiently and selectively separated from complex biological samples, thereby improving accuracy and consistency, reducing matrix effects, and providing feasibility for automated operations; the bottleneck problems in the prior art can be solved, thereby providing reliable technical support for rapid and high-efficiency analysis of TDM samples.

To improve the efficiency of pretreatment for TDM and improve the automation level when ensuring the accuracy of monitoring results, in the present application, an original phospholipid depletion magnetic bead is used for sample pretreatment. The phospholipid depletion magnetic bead can be used alone or simultaneously in combination with a to-be-detected drug-adsorption magnetic bead, such that the processes of sample extraction and impurity removal are carried out simultaneously. Moreover, the pretreatment process can be fully automated using a magnetic bead pretreatment instrument, which is suitable for synchronous selective extraction of multiple drugs, thereby significantly improving the efficiency of sample pretreatment. Up to hundreds of drugs can be extracted at a time, such that human operational errors can be reduced while the detection efficiency is greatly improved, the process for TDM is simpler and more convenient, and the monitoring precision is also improved.

The surface of the phospholipid depletion magnetic bead is modified with a functional group or molecule capable of specifically binding to phospholipids, and can selectively bind to the phospholipids in the sample, to form a magnetic bead-phospholipid complex. Under the action of an external magnetic field, the magnetic bead-phospholipid complex is rapidly separated, while unbound substances remain in the solution, thereby achieving separation and high-throughput, fully automated sample treatment.

Further, the kit further includes a to-be-detected drug-adsorption magnetic bead solution, wherein the to-be-detected drug-adsorption magnetic bead solution and the phospholipid depletion magnetic bead solution are combined into a mixed magnetic bead solution; and the to-be-detected drug-adsorption magnetic bead solution includes a magnetic bead for adsorbing and extracting a drug to be detected from the sample.

It can be understood that the phospholipid depletion magnetic bead and the to-be-detected drug-adsorption magnetic bead may be used alone sequentially, for instance, first removing phospholipids followed by adsorbing the drug to be detected, or used in combination. In the present application, preferably, the phospholipid depletion magnetic bead and the to-be-detected drug-adsorption magnetic bead are combined into a mixed magnetic bead solution for simultaneous use, which not only simplifies operational procedures but also improves the effects of adsorbing the drug to be detected and removing phospholipids.

Further, a phospholipid depletion magnetic bead includes any one or more of a phospholipid removal magnetic bead, a mixed-mode magnetic bead, a $TiO_2$ silica magnetic bead, and a $ZrO_2$ silica magnetic bead.

Further, a to-be-detected drug-adsorption magnetic bead includes any one or more of a C18 magnetic bead, a C8 magnetic bead, a phenyl magnetic bead, a silica magnetic bead, a polystyrene (PS) magnetic bead, a hydrophilic-lipophilic balance (HLB) magnetic extraction bead, a mixed-mode anion exchange (MAX) magnetic bead, and a mixed-mode cation exchange (MCX) magnetic bead.

Further, a phospholipid depletion magnetic bead in the mixed magnetic bead solution includes a $ZrO_2$ silica magnetic bead, and a to-be-detected drug-adsorption magnetic bead includes an HLB magnetic extraction bead.

When the phospholipid depletion magnetic bead and the to-be-detected drug-adsorption magnetic bead are used simultaneously, mutual interference may occur, mainly due to the following reasons: 1. competitive binding: the two types of magnetic beads may competitively bind to the same molecules, leading to the decreased recovery of the target substance; 2. steric hindrance: a large number of magnetic beads may cause steric hindrance, affecting the effective binding between the target substance and the magnetic beads; 3. non-specific adsorption: the phospholipid depletion magnetic bead may non-specifically adsorb the drug to be detected, or the to-be-detected drug-adsorption magnetic bead may non-specifically adsorb phospholipids, affecting experimental results; 4. separation efficiency: the differences in the physical properties of the two types of magnetic beads may lead to reduced separation efficiency, affecting the recovery and purity of the target substance. Therefore, it is required to select appropriate magnetic bead characteristics (including appropriate surface modifications and appropriate particle sizes) and screen appropriate pretreatment conditions to eliminate mutual interference, thereby reducing influences.

Research proves that using the combination of the phospholipid depletion magnetic bead with a surface bonded with $ZrO_2$ linked to silica and the HLB magnetic extraction bead for sample pretreatment for TDM, due to the strong binding specificity between the two types of magnetic bead, mutual interference can be effectively prevented, the problems of competitive binding and non-specific adsorption are avoided, the steric hindrance is small, and the separation efficiency is high, such that the pretreatment effect can be significantly improved, and the accuracy of detection results of the therapeutic drugs can be improved.

Further, the drug to be detected includes any one or more of a sedative-hypnotic drug, an antidepressant drug, an antipsychotic drug, an antiepileptic drug, an antibiotic drug, an antineoplastic drug, a cardiovascular drug, and a toxicology screening drug.

Research proves that the mixed magnetic bead pretreatment method provided by the present application is suitable for the simultaneous selective extraction of most drugs, mainly including a sedative-hypnotic drug, an antidepressant drug, an antipsychotic drug, an antiepileptic drug, an antibiotic drug, an antineoplastic drug, a cardiovascular drug, and a toxicology screening drug.

Further, the sedative-hypnotic drug includes any one or more of alprazolam, clonazepam, midazolam, lorazepam, zopiclone, temazepam, bromazepam, nitrazepam, 6-hydroxybuspirone, buspirone, zaleplon, memantine, donepezil, tandospirone, diazepam, nordazepam, oxazepam, zolpidem, and estazolam;

the antidepressant drug comprises any one or more of sertraline, fluoxetine, norfluoxetine, escitalopram, fluvoxamine, paroxetine, venlafaxine, O-demethylvenlafaxine, duloxetine, mirtazapine, trazodone, milnacipran, amitriptyline, nortriptyline, doxepin, vortioxetine, norclomipramine, clomipramine, agomelatine, bupropion, mianserin, nordexepin, and hydroxybupropion;

the antipsychotic drug comprises any one or more of olanzapine, clozapine, paliperidone, risperidone, dehydro-aripiprazole, aripiprazole, amisulpride, quetiapine, chlorpromazine, ziprasidone, norclozapine, haloperidol, perphenazine, sulpiride, norquetiapine, fluphenazine, thioridazine, tomoxetine, lurasidone, blonaserin, maprotiline, methylphenidate, rivastigmine, perospirone, norolanzapine, carbamazepine-10,11-epoxide, norsertraline, norcitalopram, and normirtazapine;

the antiepileptic drug comprises any one or more of oxcarbazepine, lamotrigine, levetiracetam, 10-OH Car, carbamazepine, phenytoin sodium, topiramate, primidone, gabapentin, pregabalin, rufinamide, striripentol, perampanel, zonisamide, lacosamide, valproic acid, and phenobarbital;

the antibiotic drug comprises any one or more of moxifloxacin, vancomycin, tigecycline, norvancomycin, polymyxin, linezolid, ciprofloxacin, sufamethoxazole, and levofloxacin;

the antineoplastic drug comprises any one or more of cyclophosphamide, ifosfamide, methotrexate, 5-fluorouracil, capecitabine, irinotecan, paclitaxel, docetaxel, afatinib, rivoceranib, icotinib, erlotinib, gefitinib, crizotinib, regorafenib, vemurafenib, imatinib, N-desmethylimatinib, alectinib, and osimertinib;

the cardiovascular drug comprises any one or more of metoprolol, bisoprolol, nifedipine, amlodipine, atorvastatin, ortho-hydroxyatorvastatin, rosuvastatin, losartan, losartan-metabolite, valsartan, irbesartan, telmisartan, clopidogrel-metabolite, salicylic acid, ticagrelor, and ticagrelor-metabolite M8; and the toxicology screening drug includes any one or more of rodenticides (brodifacoum, bromadiolone, diphacinone, chlorophacinone, warfarin, flocoumafen, coumatetralyl, fluoroacetic acid, difenacoum, pindone, difethialone, coumafuryl, coumachlor, and melitoxin), pesticides (199 types), psychotropic drugs (piroxicam, 4-acetamidophenol, ethenzamide, paracetamol, sulindac, dihydroergotamine, ketorolac, ketoprofen, isopropylantipyrine, difenidol, loxapine, penfluridol, trihexylphenedyl, naproxen, N,N-diethylnicotinamide, benzolyecgonine, buprenorphine, fentanyl, flunitrazepam, ropivacaine, pethidine, procaine, oxycodone, tramadol, normorphine, ethylmorphine, dextropropoxyphene, and lidocaine), and biotoxins (aconitine, solanine, colchicine, amygdalin, ouabain octahydrate, tetrodotoxin, (+)-muscarine, and aflatoxin).

The method provided by the present application enables simultaneous pretreatment and detection of over 300 therapeutic drugs.

Further, the mixed magnetic bead solution includes an acid, and the acid includes any one or more of formic acid, acetic acid, and citric acid.

The surface of the HLB magnetic extraction bead includes specific proportions of hydrophilic and hydrophobic groups: the hydrophobic divinylbenzene structure retains a nonpolar compound, the hydrophilic N-vinylpyrrolidone structure retains a polar compound, showing good applicability. However, considering significant differences in the polarity and acid-base properties of different drugs, to achieve optimal extraction efficiency and good applicability, strict control of solution acid-base properties or organic phase ratio is required during extraction using the HLB magnetic extraction bead.

In some embodiments, the ionization of acidic compounds can be suppressed by adding an acid, thereby improving the extraction efficiency of the HLB magnetic extraction bead for acidic drugs such as valproic acid and methotrexate. Valproic acid, a common antiepileptic drug, with Pka of 4.6 (at 25° C.), exists in a fully ionized state in the neutral environment of serum, and cannot retain on the HLB magnetic extraction bead, resulting in very low extraction efficiency. By adding a specific concentration of acid into the solution, the ionization of carboxyl is suppressed to maintain the neutral molecular state, thereby significantly improving the extraction efficiency of the HLB magnetic extraction bead.

In some embodiments, the binding between drugs and proteins can also be adjusted by means of the acid-base changes, facilitating the extraction process of drugs. For instance, vemurafenib, an antineoplastic drug, has a binding rate of >99% to plasma proteins such as human albumin and α-1 acid glycoprotein after absorption, and is nearly insoluble in water. Hydrogen bonds within protein molecules are changed by means of acid adjustment, reducing the binding effect of vemurafenib to proteins and promoting the migration of the drug to the HLB material.

In addition, surprisingly, in mixed magnetic beads, acid not only facilitates drug adsorption and extraction but also facilitates the phospholipid depletion magnetic bead to more efficiently exert the effect of phospholipid adsorption, thereby effectively reducing the matrix effect and ensuring the accuracy of detection results. However, if phosphoric acid is used in this process, the effect of phospholipid adsorption of the phospholipid depletion magnetic bead will be reduced; meanwhile, the phospholipids in the sample are non-specifically adsorbed onto the surface of the HLB magnetic extraction bead. Thus, the addition of an acidic substance being not phosphoric acid is required during extraction.

Further, the acid has a mass concentration of 0.1%-2%.

In some embodiments, preferably, 1% formic acid (FA) or 1 M citric acid (CA) is added into a diluent.

Further, the kit further includes an eluent, wherein the eluent includes methanol with formic acid.

Since the eluent simultaneously elutes the mixed magnetic beads, it must smoothly elute the drug to be detected from the to-be-detected drug-adsorption magnetic bead, but cannot elute phospholipids from the phospholipid depletion magnetic bead; moreover, the elution process of the drug to be detected cannot be affected by the phospholipid depletion magnetic bead, thereby preventing cross-influence and improving the specific elution effect. It can be seen that the use of an appropriate eluent also facilitates the accuracy and sensitivity of detection results to be improved. In the elution process after mixed magnetic bead adsorption and extraction, acid facilitates the elution efficiency of analytes to be improved. However, in the process of evaluating the influences of different acids during elution, it is found that if phosphoric acid is added during elution, the phospholipid content in the eluent will be increased, affecting the service life of the chromatographic column and contaminating the mass spectrometry detector. Thus, not using phosphoric acid is required in the eluent.

In some embodiments, preferably, methanol with 0.1% formic acid is used as an eluent.

Further, the kit further includes an equilibrium solution, a diluent, and liquid chromatography mobile phases, wherein both the equilibrium solution and the diluent are aqueous formic acid solutions; the liquid chromatography mobile phases include mobile phase A and mobile phase B; the mobile phase A is an aqueous solution containing a mobile phase additive; the mobile phase B is a methanol solution containing a mobile phase additive; and the mobile phase additive is one or a mixture of formic acid and ammonium acetate.

In another aspect, the present application provides a method for drug detection. The method is based on non-disease diagnosis purposes, and includes the following steps:

(1) treating a sample with a mixed magnetic bead solution, wherein the mixed magnetic bead solution includes a phospholipid depletion magnetic bead and a to-be-detected drug-adsorption magnetic bead, such that phospholipids and a drug to be detected in the sample are simultaneously adsorbed; and (2) eluting the drug to be detected with an eluent, and analyzing a content of the drug to be detected by liquid chromatography-tandem mass spectrometry, wherein the drug to be detected comprises any one or more of a sedative-hypnotic drug, an antidepressant drug, an antipsychotic drug, an antiepileptic drug, an antibiotic drug, an antineoplastic drug, a cardiovascular drug, and a toxicology screening drug.

Further, the mixed magnetic bead solution in step (1) includes an acid, and the acid includes any one or more of formic acid, acetic acid, and citric acid; and the eluent in step (2) includes methanol with formic acid.

The TDM analysis technology based on the magnetic bead method and LC-MS/MS provided by the present application can achieve simultaneous monitoring of over 300 therapeutic drugs through the simplest and most efficient operational process, thereby effectively eliminating the matrix effect and human-induced interferences, and ensuring the accuracy and sensitivity of monitoring results.

In yet another aspect, the present application provides a system for therapeutic drug monitoring, including: a drug detection module, a data input/output interface, and a data analysis module, wherein the drug detection module obtains a detection value of a substance to be detected using the aforementioned method; the data input/output interface is configured to input a detection value of at least one drug; the data analysis module is configured to analyze the detection value of the drug, and the drug includes any one or more of a sedative-hypnotic drug, an antidepressant drug, an antipsychotic drug, an antiepileptic drug, an antibiotic drug, an antineoplastic drug, a cardiovascular drug, and a toxicology screening drug; and after analysis by the data analysis module, the data input/output interface is configured to output situations of therapeutic drug monitoring results relative to a drug effective concentration range.

In yet another aspect, the present application provides use of a mixed magnetic bead solution in preparing a reagent for improving accuracy of therapeutic drug monitoring, wherein the mixed magnetic bead solution includes a phospholipid depletion magnetic bead solution and a to-be-detected drug-adsorption magnetic bead solution; the phospholipid depletion magnetic bead solution includes a magnetic bead for removing phospholipids in a sample; and the to-be-detected drug-adsorption magnetic bead solution includes a magnetic bead for adsorbing and extracting a drug to be detected from the sample.

Further, a phospholipid depletion magnetic bead includes a $ZrO_2$ silica magnetic bead, and a to-be-detected drug-adsorption magnetic bead includes an HLB magnetic extraction bead.

The kit for therapeutic drug monitoring and the method and system thereof constructed in the present application have the following beneficial effects:

1. By using the automated mixed magnetic bead extraction process, thorough removal of impurities (proteins, phospholipids, salts, etc.) and purification of samples can be achieved, thereby reducing the matrix effect, shortening single-injection sample analysis time, improving detection efficiency, prolonging the service life of chromatographic column, and improving the accuracy of detection results, and solving the problems of the protein precipitation method in existing TDM analysis technologies, such as difficult impurity removal, high matrix effects, and chromatographic column prone to injury.
2. By using the mixed magnetic bead extraction combined with LC-MS/MS for TDM, the pretreatment and analytical methods flexible to and compatible with hundreds of drugs are rapidly and efficiently established, and the automation degree is high, thereby eliminating human errors and inconsistency between batches; the high specificity of the detection method can eliminate cross-reactivity between metabolites and parent drugs, facilitating the new drug development process and being suitable for concentration detection for hundreds of drugs.
3. The sample concentration in the treatment process using the protein precipitation method in the prior art is indiscriminately diluted, the detection sensitivity for certain drugs is affected, and further nitrogen blowdown concentration of supernatant and reconstitution are required before injection, resulting in time and labor consuming in pretreatment; in the process of automated magnetic bead pretreatment of samples, the sensitivity and concentration information of the detected drugs can be taken into account simultaneously; the sample is diluted or enriched by adjusting the volume of the eluent, particularly for the situations requiring concentration of the drug to be detected, such as toxicology screening, significantly improving pretreatment and detection efficiency, with very strong adaptability.

4. The combination of the magnetic bead with a surface bonded with an HLB silica material and the phospholipid depletion magnetic bead is screened for adsorption and extraction of drugs to be detected in serum samples to be detected. In conjunction with automated treatment equipment, the pretreatment efficiency is high, phospholipid interference is less, and the extraction efficiency for some drugs is superior to that of the traditional protein precipitation method. The pretreatment time for treating 96 test samples is only 8 minutes, without the need for a vortex mixer or a centrifuge.
5. In this technical solution, a pre-packaged kit for in-vitro diagnosis TDM is filed, and the filed Class I kit includes a magnetic bead suspension, an activation solution, a sample diluent (with an internal standard), a leaching solution, and an eluent. Before TDM analysis, only by peeling off the sealing film of the pre-packaged kit, respectively adding the appropriate amount of sample to be detected/calibrator/control material to sample diluents at different wells of the pre-packaged kit, and initiating the automated extraction process of a magnetic bead instrument, the eluent can be obtained after 8 minutes. The suitable magnetic bead extraction instrument and the size of the pre-packaged kit can be selected according to the volume of samples, which can extract up to 32, 48, and 96 samples once.

DETAILED DESCRIPTION OF THE INVENTION

Figure 1:
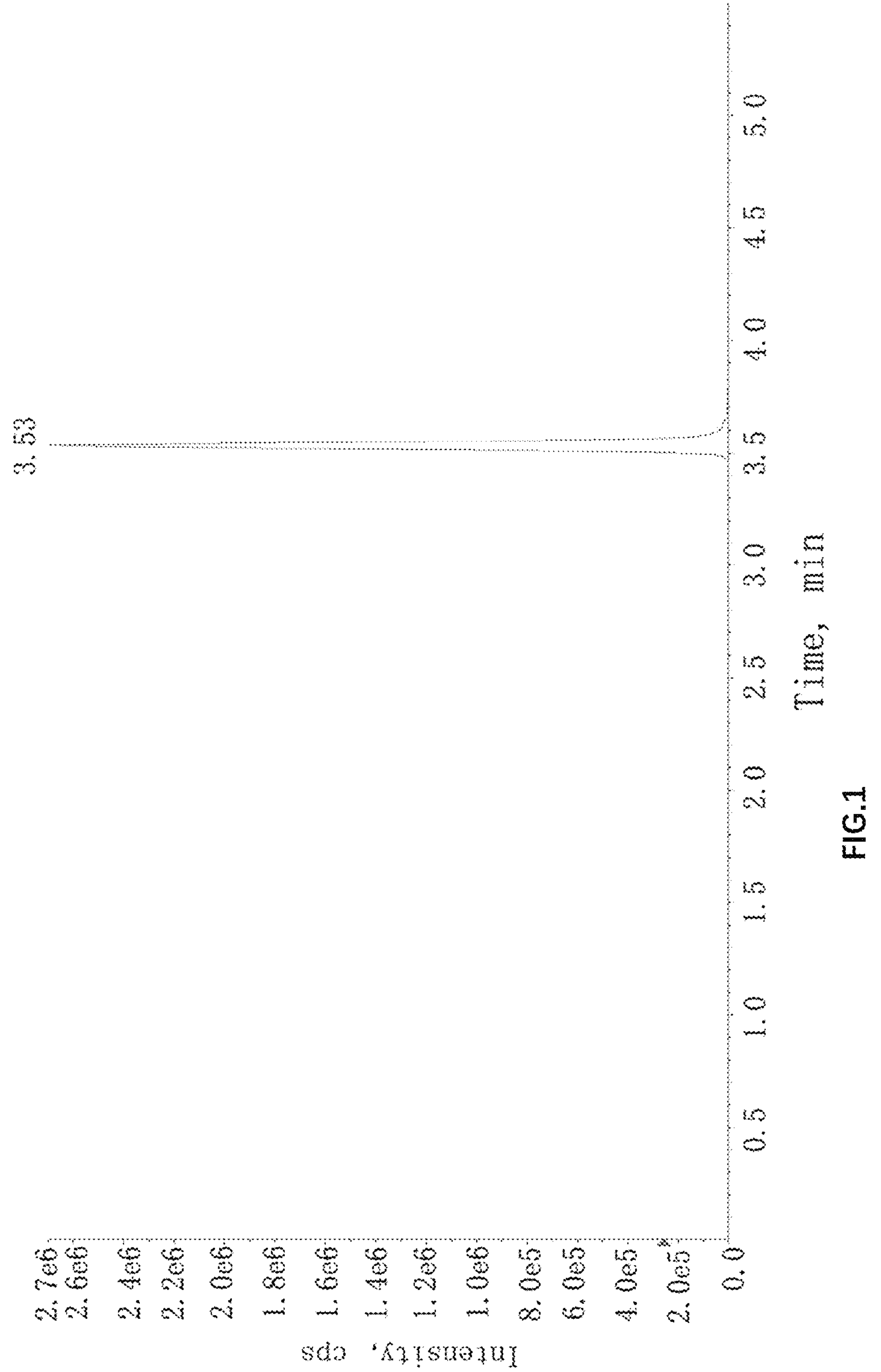
FIG. 1 shows detection chromatograms of carbamazepine.

To describe the present application more specifically, the technical solutions of the present application are described in detail below in conjunction with the drawings and specific embodiments. These descriptions are merely illustrative of how the present application may be implemented and should not be construed as limiting the specific scope of the present application. The scope of the present application is defined in the claims.

Example 1: Method for TDM Using Magnetic Bead Method Combined with LC-MS/MS Detection I. Solution Preparation:

Magnetic bead suspension: weighing 1 g of HLB magnetic extraction beads (Supplier: 3P Biosolutions, Cat. No. MB001-1; particle size: 20-40 μm, specific surface area: about 600-750 $m^2/g$; pore size: about 80 A), and adding the HLB magnetic extraction beads to 100 mL of 50% ethanol to prepare a 10 mg/mL HLB magnetic bead suspension, stored at 2-8° C.

Phospholipid depletion magnetic beads: weighing 1 g of phospholipid depletion magnetic beads (Supplier: 3P Biosolutions, Cat. No. MB003-1; particle size: 20-40 μm, specific surface area: about 600-750 $m^2/g$; pore size: about 80 A), and adding the phospholipid depletion magnetic beads to 100 mL of methanol to prepare a 10 mg/mL phospholipid depletion magnetic bead suspension, stored at 2-8° C.

Mixed magnetic bead solution: taking 1 mL of the HLB magnetic extraction bead suspension and 1 mL of the phospholipid depletion magnetic bead suspension, and mixing uniformly to obtain a mixed magnetic bead solution.

Equilibrium solution: pipetting 1 mL of formic acid to be added into 1,000 mL of ultrapure water and mixing uniformly to obtain an equilibrium solution, stored at 2-8° C.

Diluent: pipetting 1 mL of formic acid to be added into 1,000 mL of ultrapure water and mixing uniformly to obtain a diluent, stored at 2-8° C.

Leaching solution 1/Leaching solution 2: ultrapure water.

Eluent: methanol with 0.1% formic acid.

II. Sample Detection:

1. Pretreatment with Magnetic Bead Method (1) Sample addition: adding 20 μL of a calibrator, a control material, or a sample to be detected to Column 3/9 in a 96-well plate, followed by 200 μL of an internal standard-containing diluent.

(2) Pretreatment reagent addition: sequentially adding 200 μL of the magnetic bead suspension, 200 μL of the equilibrium solution, 200 μL of leaching solution 1, 200 μL of leaching solution 2, and 100 μL of the eluent according to Table 1.

TABLE 1

Placement Positions of Pretreatment Reagents

| Column 1 (7) | Column 2 (8) | Column 3 (9) | Column 4 (10) | Column 5 (11) | Column 6 (12) |
|---|---|---|---|---|---|
| Magnetic bead suspension | Equilibrium solution | Sample | Leaching solution 1 | Leaching solution 2 | Eluent |
| Magnetic bead suspension | Equilibrium solution | Sample | Leaching solution 1 | Leaching solution 2 | Eluent |

TABLE 1-continued

Placement Positions of Pretreatment Reagents

| Column 1 (7) | Column 2 (8) | Column 3 (9) | Column 4 (10) | Column 5 (11) | Column 6 (12) |
|---|---|---|---|---|---|
| Magnetic bead suspension | Equilibrium solution | Sample | Leaching solution 1 | Leaching solution 2 | Eluent |
| Magnetic bead suspension | Equilibrium solution | Sample | Leaching solution 1 | Leaching solution 2 | Eluent |
| Magnetic bead suspension | Equilibrium solution | Sample | Leaching solution 1 | Leaching solution 2 | Eluent |
| Magnetic bead suspension | Equilibrium solution | Sample | Leaching solution 1 | Leaching solution 2 | Eluent |
| Magnetic bead suspension | Equilibrium solution | Sample | Leaching solution 1 | Leaching solution 2 | Eluent |
| Magnetic bead suspension | Equilibrium solution | Sample | Leaching solution 1 | Leaching solution 2 | Eluent |

(3) Placing a 96-well plate into an automated magnetic bead extraction instrument for sample extraction. The operating procedures of the magnetic bead extraction instrument are shown in Table 2. The pretreatment time for the samples per batch is 8 minutes. The current magnetic bead extraction instrument used can accommodate two 96-well plates at a time for parallel operation, with a pretreatment throughput of 32 samples per batch.

TABLE 2

Operating Procedures of Magnetic Bead Extraction Instrument

| No. | Instruction | 96-well Plate Column | Mixing Time (S) | Solvent Volume (μL) | Magnetic Adsorption Time (S) |
|---|---|---|---|---|---|
| 1 | Activation | 1 (7) | 30 | 100 | 30 |
| 2 | Activation | 2 (8) | 30 | 200 | 30 |
| 3 | Loading | 3 (9) | 60 | 200 | 30 |
| 4 | Leaching | 4 (10) | 30 | 200 | 30 |
| 5 | Leaching | 5 (11) | 30 | 200 | 30 |
| 6 | Elution | 6 (12) | 60 | 100 | 30 |
| 7 | Waste removal | 1 (7) | 10 | 100 | 0 |

The main steps include:

Step 1: placing a magnetic rod into an activation tube for up-and-down stirring to activate magnetic beads to be adsorbed to the surface of the magnetic rod, and preparing for subsequent operations.

Step 2: transferring a separation magnetic bead material carried by the magnetic rod to a sample tube, continuing up-and-down stirring to ensure thorough mixing of the magnetic bead material with a sample, and adsorbing and extracting a target substance and impurities.

Step 3: transferring the magnetic bead material adsorbing the target substance and the impurities carried by the magnetic rod to a leaching tube, and carrying out leaching by up-and-down stirring to remove the impurities.

Step 4: transferring the magnetic bead material adsorbing the target substance carried by the magnetic rod to an elution tube, and carrying out up-and-down stirring to achieve elution to separate and wash the target substance.

Step 5: using the magnetic rod to adsorb and remove residual separation magnetic beads and phospholipid depletion magnetic bead material, and transferring same to a waste well (original activation tube) to complete the entire pretreatment extraction process.

(4) After the completion of extraction using the magnetic bead extraction instrument, pipetting 40 μL of the eluent from Columns 6 and 12 of the 96-well plate to be transferred to a 96-well loading plate, adding 160 μL of ultrapure water, and carrying out uniform vortex mixing and on-machine detection.

2. LC-MS/MS Detection

When carrying out LC-MS/MS analysis, gradient elution was used for liquid chromatography. The separation conditions for analytes were established using reversed phase chromatography as follows: a chromatographic column was DISIGNS Column-003, 2.6 μm, 50*3 mm, with a flow rate of 0.7 mL/min and a column temperature of 40° C., wherein mobile phase A was an aqueous solution containing a mobile phase additive, and mobile phase B was a methanol solution containing mobile phase additive. The gradient program is shown in Table 3.

TABLE 3

Gradient Elution Program

| Time (min) | Flow Rate (mL/min) | Mobile Phase A (%) | Mobile Phase) B (% |
|---|---|---|---|
| 0 | 0.7 | 95 | 5 |
| 0.2 | 0.7 | 95 | 5 |
| 0.3 | 0.7 | 75 | 25 |
| 2 | 0.7 | 65 | 35 |
| 4.8 | 0.7 | 15 | 85 |
| 4.9 | 0.7 | 0 | 100 |
| 5.5 | 0.7 | 0 | 100 |
| 5.6 | 0.7 | 95 | 5 |
| 6 | 0.7 | 95 | 5 |

When carrying out mass spectrometry detection, a triple quadrupole mass spectrometer (model: CalQuant-U independently developed by CALIBRA) was used for quantitative detection, and the positive and negative ion modes of an electrospray ionization source and a multiple reaction monitoring (MRM) mode were used for mass spectrometry detection. The corresponding mass spectrometry parameters are shown in Table 4.

TABLE 4

| Mass Spectrometry Parameters for Quantitative Detection of Drugs | | | | |
|---|---|---|---|---|
| Drug Name | Analyte Name ID | Internal Standard Parent Ion Q1 | Internal Standard Daughter Ion Q3 | Internal Standard ID |
| Alprazolam | Alprazolam | 314.1 | 210 | Alprazolam-IS |
| Clonazepam | Clonazepam | 319.8 | 274 | Clonazepam-IS |
| Midazolam | Midazolam | 330.1 | 295 | Midazolam-IS |
| Lorazepam | Lorazepam | 325 | 233 | Lorazepam-IS |
| Zopiclone | Zopiclone | 397 | 244.9 | Zopiclone-IS |
| Temazepam | Temazepam | 306.1 | 260.1 | Temazepam-IS |
| Bromazepam | Bromazepam | 320 | 213 | Bromazepam-IS |
| Nitrazepam | Nitrazepam | 287.3 | 185.2 | Nitrazepam-IS |
| 6-Hydroxybuspirone | 6-Hydroxybuspirone | 410.3 | 122.2 | 6-Hydroxybuspirone-IS |
| Buspirone | Buspirone | 394.5 | 121.9 | Buspirone-IS |
| Zaleplon | Zaleplon | 311 | 269.1 | Zaleplon-IS |
| Memantine | Memantine | 186.2 | 110.2 | Memantine-IS |
| Donepezil | Donepezil | 387.2 | 98 | Donepezil-IS |
| Tandospirone | Tandospirone | 392.4 | 122.1 | Tandospirone-IS |
| Diazepam | Diazepam | 290 | 198 | Diazepam-IS |
| Nordazepam | Nordazepam | 276.1 | 213.1 | Nordazepam-IS |
| Oxazepam | Oxazepam | 292 | 162.9 | Oxazepam-IS |
| Zolpidem | Zolpidem | 315.2 | 242.1 | Zolpidem-IS |
| Estazolam | Estazolam | 299.9 | 271.9 | Estazolam-IS |
| Sertraline | Sertraline | 309.1 | 275.1 | Sertraline-IS |
| Fluoxetine | Fluoxetine | 315.2 | 44 | Fluoxetine-IS |
| Norfluoxetine | Norfluoxetine | 301 | 139.2 | Norfluoxetine-IS |
| Escitalopram | Escitalopram | 331.3 | 109.2 | Escitalopram-IS |
| Fluvoxamine | Fluvoxamine | 323.3 | 70.9 | Fluvoxamine-IS |
| Paroxetine | Paroxetine | 334.3 | 196.2 | Paroxetine-IS |
| Venlafaxine | Venlafaxine | 284.2 | 121.3 | Venlafaxine-IS |
| O-Demethyl-Venlafaxine | O-Demethyl-Venlafaxine | 267 | 106.9 | O-Demethyl-Venlafaxine-IS |
| Duloxetine | Duloxetine | 305.1 | 154 | Duloxetine-IS |
| Mirtazapine | Mirtazapine | 269.3 | 195 | Mirtazapine-IS |
| Trazodone | Trazodone | 378.3 | 150.2 | Trazodone-IS |
| Milnacipran | Milnacipran | 252.2 | 235.1 | Milnacipran-IS |
| Amitriptyline | Amitriptyline | 284.2 | 233.2 | Amitriptyline-IS |
| Nortriptyline | Nortriptyline | 267.2 | 233.1 | Nortriptyline-IS |
| Doxepin | Doxepin | 283.3 | 107 | Doxepin-IS |
| Vortioxetine | Vortioxetine | 307.2 | 153 | Vortioxetine-IS |
| Norclomipramine | Norclomipramine | 304 | 75.1 | Norclomipramine-IS |
| Clomipramine | Clomipramine | 318.2 | 89.2 | Clomipramine-IS |
| Agomelatine | Agomelatine | 250.2 | 188 | Agomelatine-IS |
| Bupropion | Bupropion | 249.2 | 185 | Bupropion-IS |
| Mianserin | Mianserin | 268.3 | 208.3 | Mianserin-IS |
| Nordexepin | Nordexepin | 269.1 | 235.3 | Nordexepin-IS |
| Hydroxybupropion | Hydroxybupropion | 262.2 | 139.2 | Hydroxybupropione-IS |
| Olanzapine | Olanzapine | 321.1 | 261.1 | Olanzapine-IS |
| Clozapine | Clozapine | 335.2 | 275 | Clozapine-IS |
| Paliperidone | Paliperidone | 431.2 | 114.1 | Paliperidone-IS |
| Risperidone | Risperidone | 415.2 | 195.3 | Risperidone-IS |
| Dehydro-Aripiprazole | Dehydro-Aripiprazole | 454.2 | 293 | Dehydro-Aripiprazole-IS |
| Aripiprazole | Aripiprazole | 456.2 | 293 | Aripiprazole-IS |
| Amisulpride | Amisulpride | 375.2 | 242.1 | Amisulpride-IS |
| Quetiapine | Quetiapine | 392.2 | 258.2 | Quetiapine-IS |
| Chlorpromazine | Chlorpromazine | 325 | 246 | Chlorpromazine-IS |
| Ziprasidone | Ziprasidone | 421.2 | 194.2 | Ziprasidone-IS |
| Norclozapine | Norclozapine | 321.1 | 274.2 | Norclozapine-IS |
| Haloperidol | Haloperidol | 380.1 | 165.3 | Haloperidol-IS |
| Perphenazine | Perphenazine | 412.1 | 179.2 | Perphenazine-IS |
| Sulpiride | Sulpiride | 345.2 | 217.1 | Sulpirde-IS |
| Norquetiapine | Norquetiapine | 304.2 | 208.9 | Norquetiapine-IS |
| Fluphenazine | Fluphenazine | 446.2 | 179.2 | Fluphenazine-IS |
| Thioridazine | Thioridazine | 375.3 | 130.3 | Thioridazine-IS |
| Tomoxetine | Tomoxetine | 259.2 | 151.3 | Tomoxetine-IS |
| Lurasidone | Lurasidone | 501.2 | 166.2 | Lurasidone-IS |
| Blonaserin | Blonaserin | 373.3 | 297.1 | Blonaserin-IS |
| Maprotiline | Maprotiline | 281 | 219.1 | Maprotiline-IS |
| Methylphenidate | Methylphenidate | 236.9 | 84 | Methylphenidate-IS |
| Rivastigmine | Rivastigmine | 254.9 | 206.1 | Rivastigmine-IS |
| Perospirone | Perospirone | 435.1 | 177.1 | Perospirone-IS |
| Norolanzapine | NorOlanzapine | 307.1 | 198 | NorOlanzapine-IS |
| Carbamazepine-10,11-epoxide | Carbamazepine-10,11-epoxide | 263 | 246.1 | Carbamazepine-10,11-epoxide-IS |
| Norsertraline | NorSertraline | 281.1 | 159 | NorSertraline-IS |
| Norcitalopram | NorCitalopram | 314.2 | 109.1 | NorCitalopram-IS |
| Normirtazapine | NorMirtazapine | 256.2 | 195.1 | NorMirtazapine-IS |

TABLE 4-continued

| Mass Spectrometry Parameters for Quantitative Detection of Drugs | | | | |
|---|---|---|---|---|
| Drug Name | Analyte Name ID | Internal Standard Parent Ion Q1 | Internal Standard Daughter Ion Q3 | Internal Standard ID |
| Cyclophosphamide | Cyclophosphamide | 269 | 147 | Cyclophosphamide-IS |
| Ifosfamide | Ifosfamide | 265.2 | 78 | Ifosfamide-IS |
| Methotrexate | Methotrexate | 458.2 | 310.9 | Methotrexate-IS |
| Capecitabine | Capecitabine | 371.3 | 255.1 | Capecitabine-IS |
| Irinotecan | Irinotecan | 587.185 | 195.1 | Irinotecan-IS |
| Paclitaxel | Paclitaxel | 881.2 | 312.8 | Paclitaxel-IS |
| Docetaxel | Docetaxel | 839.3 | 549.1 | Docetaxel-IS |
| Afatinib | Afatinib | 492 | 371 | Afatinib-IS |
| Rivoceranib | Rivoceranib | 406.3 | 212 | Rivoceranib-IS |
| Icotinib | Icotinib | 396.1 | 304 | Icotinib-IS |
| Erlotinib | Erlotinib | 400 | 278.1 | Erlotinib-IS |
| Gefitinib | Gefitinib | 450 | 100 | Gefitinib-IS |
| Crizotinib | Crizotinib | 455 | 265.1 | Crizotinib-IS |
| Regorafenib | Regorafenib | 486 | 273 | Regorafenib-IS |
| Vemurafenib | Vemurafenib | 496 | 389 | Vemurafenib-IS |
| Imatinib | Imatinib | 502.2 | 394 | Imatinib-IS |
| N-Desmethylimatinib | N-Desmethylimatinib | 488.2 | 394.1 | N-Desmethylimatinib-IS |
| Alectinib | Alectinib | 491.2 | 396.1 | Alectinib-IS |
| Osimertinib | Osimertinib | 506.2 | 77.9 | Osimertinib-IS |
| Metoprolol | Metoprolol | 275.1 | 79.1 | Metoprolol-IS |
| Bisoprolol | Bisoprolol | 326.2 | 116.2 | BisoprololiIS |
| Nifedipine | Nifedipine | 351.1 | 122.1 | Nifedipine-IS |
| Amlodipine | Amlodipine | 409.2 | 238 | Amlodipine-IS |
| Atorvastatin | Atorvastatin | 557.2 | 278.3 | Atorvastatin-IS |
| Ortho-Hydroxyatorvastatin | Ortho-Hydroxyatorvastatin | 578.3 | 283.2 | Ortho-Hydroxyatorvastatin-IS |
| Rosuvastatin | Losartan | 427.1 | 211.2 | Losartan-IS |
| Losartan | Rosuvastatin | 483.2 | 421.4 | Rosuvastatin-IS |
| Losartan-metabolite | Losartan-Meta | 439 | 235 | Losartan-Meta-IS |
| Valsartan | Valsartan | 436.3 | 206.9 | Valsartan-IS |
| Irbesartan | Irbesartan | 430.2 | 195.2 | Irbesartan-IS |
| Telmisartan | Telmisartan | 518.5 | 279 | Telmisartan-IS |
| Clopidogrel-metabolite | Clopidogrel-Meta | 308.1 | 169.1 | Clopidogrel-IS |
| Salicylic acid | Salicylic acid | 140.9 | 97 | Salicylic acid-IS |
| Ticagrelor | Ticagrelor | 523.1 | 495.1 | Ticagrelor-IS |
| Ticagrelor-metabolite M8 | Ticagrelor-Meta M8 | 479.1 | 127.1 | Ticagrelor-IS |
| Lamotrigine | Lamotrigine | 256 | 145 | Lamotrigine-IS |
| 10-OH Car | 10-OH Car | 259.1 | 168.9 | 10-OH Car-IS |
| Carbamazepine | Carbamazepine | 240.2 | 180.1 | Carbamazepine-IS |
| Phenytoin Sodium | Phenytoin Sodium | 263.1 | 109.1 | Phenytoin Sodium-IS |
| Topiramate | Topiramate | 352.2 | 270.3 | Topiramate-IS |
| Primidone | Primidone | 224.3 | 167 | Primidone-IS |
| Rufinamide | Rufinamide | 242 | 109.1 | Rufinamide-IS |
| Striripentol | Striripentol | 226.2 | 195.9 | Striripentol-IS |
| Perampanel | Perampanel | 355.1 | 218.9 | Perampanel-IS |
| Zonisamide | Zonisamide | 217.2 | 135.9 | Zonisamide-IS |
| Lacosamide | Lacosamide | 255.2 | 120.1 | Lacosamide-IS |
| Valproic Acid | Valproic Acid | 149.1 | 149.1 | Valproic Acid-IS |
| Phenobarbital | Phenobarbital | 236 | 193.3 | Phenobarbital-IS |
| Donepezil | Donepezil | 380.2 | 91 | Donepezil-IS |
| Memantine | Memantine | 180.2 | 107.2 | Memantine-IS |
| Gabapentin | Gabapentin | 172.1 | 137.2 | Gabapentin-IS |
| Pregabalin | Pregabalin | 160.1 | 142.2 | Pregabalin-IS |
| Levetiracetam | Levetiracetam | 171.2 | 154.4 | Levetiracetam-IS |
| Oxcarbazepine | Oxcarbazepine | 253.3 | 180.2 | Oxcarbazepine-1 |
| Moxifloxacin | Moxifloxacin | 405.2 | 387.1 | Moxifloxacin-IS |
| Vancomycin | Vancomycin | 73 | 112 | Vancomycin-IS |
| Tigecycline | Tigecycline | 595.3 | 514.1 | Tigecycline-IS |
| Norvancomycin | Norvancomycin | 73 | 112 | Vancomycin-IS |
| Polymyxin B | Polymyxin B1 | 578.6 | 227.1 | Polymyxin E |
| Linezolid | Linezolid | 340.9 | 297.2 | Linezolid-IS |
| Sufamethoxazole | Sufamethoxazole | 258.1 | 160.1 | Sufamethoxazole-IS |
| Levofloxacin | Levofloxacin | 365.2 | 321.1 | Levofloxacin-IS |
| Polymyxin B2 | Polymyxin B2 | 578.6 | 227.1 | Polymyxin E |
| Ciprofloxacin | Ciprofloxacin | 340 | 296.1 | Ciprofloxacin-IS |
| Cefepime | Cefepime | 241 | 227 | Cefepime-IS |
| Meropenem | Meropenem | 384.165 | 141.1 | Meropenem-IS |
| Cefperazone | Cefperazone | 646.4 | 530.4 | Cefperazone-IS |
| Piperacillin | Piperacillin | 518.3 | 143.3 | Piperacillin-IS |
| Amoxicillin | Amoxicillin | 366.2 | 114.2 | Amoxicillin-IS |

TABLE 4-continued

| Mass Spectrometry Parameters for Quantitative Detection of Drugs | | | | |
|---|---|---|---|---|
| Drug Name | Analyte Name ID | Internal Standard Parent Ion Q1 | Internal Standard Daughter Ion Q3 | Internal Standard ID |
| Tazuobactam | Tazuobactam | 301 | 99 | Tazuobactam-IS |
| Imipenem | Imipenem | 300.1 | 98 | Imipenem-IS |
| Fentanyl | Fentanyl | 337.28 | 187.9 | Fentanyl-IS |
| Morphine | Morphine | 286.219 | 152.1 | Morphine-IS |
| Oxycodone | Oxycodone | 316.287 | 297.9 | Oxycodone-IS |
| 5-Fluorouracil | 5-Fluorouracil | 128.884 | 41.9 | 5-Fluorouracil-IS |
| Bisoprolol | Bisoprolol | 326.2 | 116.2 | Bisoprolol-IS |
| Indapamide | Indapamide | 366 | 132 | Indapamide-IS |
| Nimodipine | Nimodipine | 419.2 | 343.1 | Nimodipine-IS |
| Enalapril | Enalapril | 377.2 | 160.2 | Enalapril-IS |
| Perindopril | Perindopril | 369.1 | 172.1 | Perindopril-IS |
| Propranolol | Propranolol | 260 | 157 | Propranolol-IS |
| Fosinopril | Fosinopril | 514.2 | 458.2 | Fosinopril-IS |
| Captopril-disulfide | Captopril-dis | 433.3 | 216 | Captopril-dis-IS |
| Telmisartan | Telmisartan | 515.2 | 276 | Telmisartan-IS |
| Metoprolol | Metoprolol | 268.1 | 191.1 | Metoprolol-IS |
| Losartan | Losartan | 423.1 | 207.1 | Losartan-IS |
| Losartan Carboxylic Acid | Losartan-Meta | 439 | 235 | Losartan-Meta-IS |
| Irbesartan | Irbesartan | 430.2 | 195.2 | Irbesartan-IS |
| Valsartan | Valsartan | 436.3 | 206.9 | Valsartan-IS |
| 4-Valsartan | Valsartan-Meta | 452.2 | 207.1 | Valsartan-Meta-IS |
| Amlodipine | Amlodipine | 409.2 | 238 | Amlodipine-IS |
| Dehydrofelodipine | Felodipine Meta | 382 | 354 | Felodipine Meta-IS |
| Canrenone | Spironolactone-Meta | 341 | 107.1 | Spironolactone-Meta-IS |
| Captopril | Captopril | 218 | 116 | Captopril-IS |

The ion source conditions are shown in Table 5.

TABLE 5

| Ion Source Conditions | |
|---|---|
| Ion Source Condition | Value |
| Curtain Gas (CUR) | 30 psi |
| Ion Source Gas1 (GS1) | 55 psi |
| Ion Source Gas2 (GS2) | 55 psi |
| Ion Source Heating Temperature | 500° C. |

TABLE 5-continued

| Ion Source Conditions | |
|---|---|
| Ion Source Condition | Value |
| Collision Gas (CAD) | 10 psi |
| IonSpray Voltage | 5500 V/−4500 V |

Figure 2:
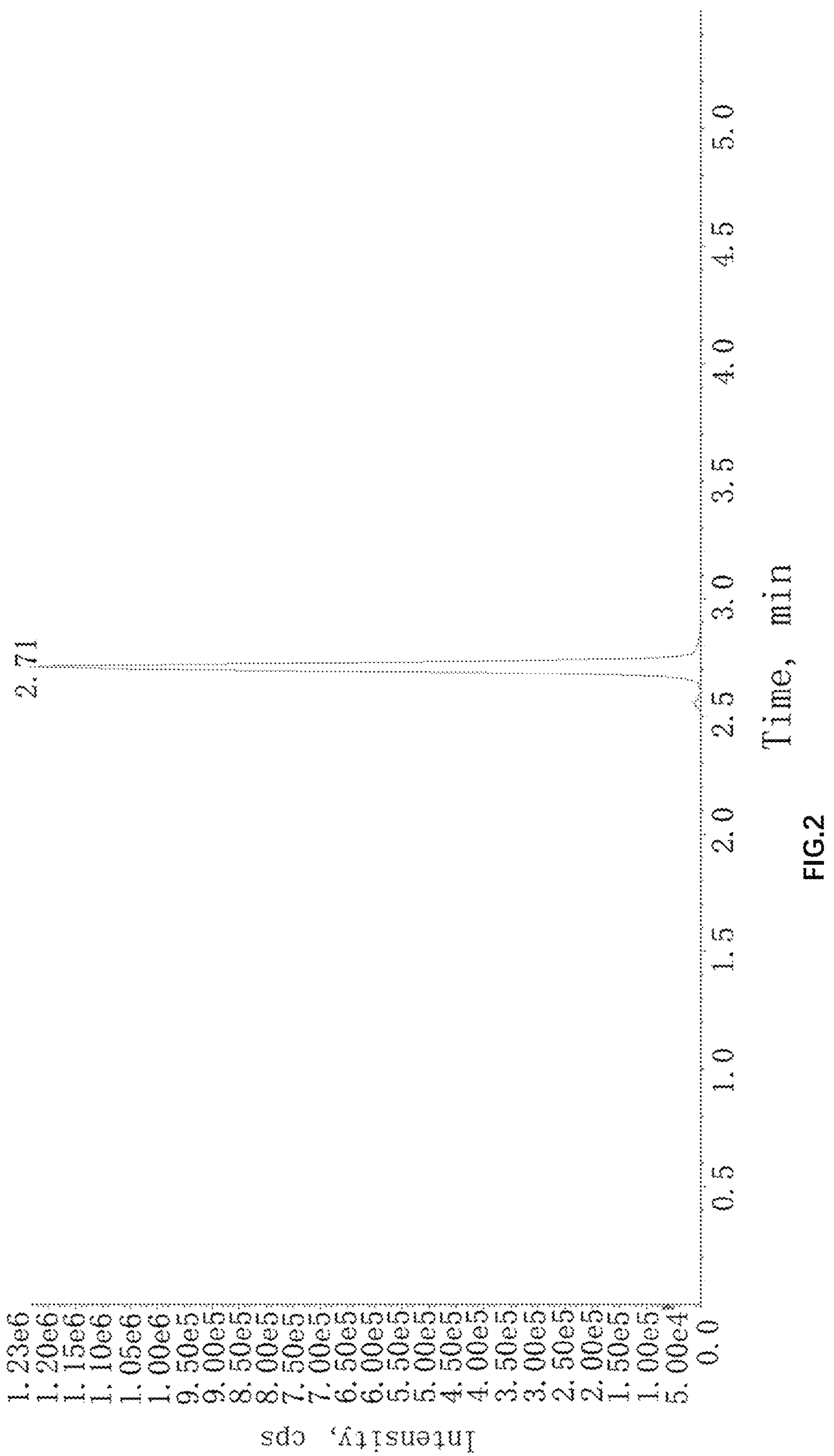
FIG. 2 shows detection chromatograms of cyclophosphamide.
Figure 3:
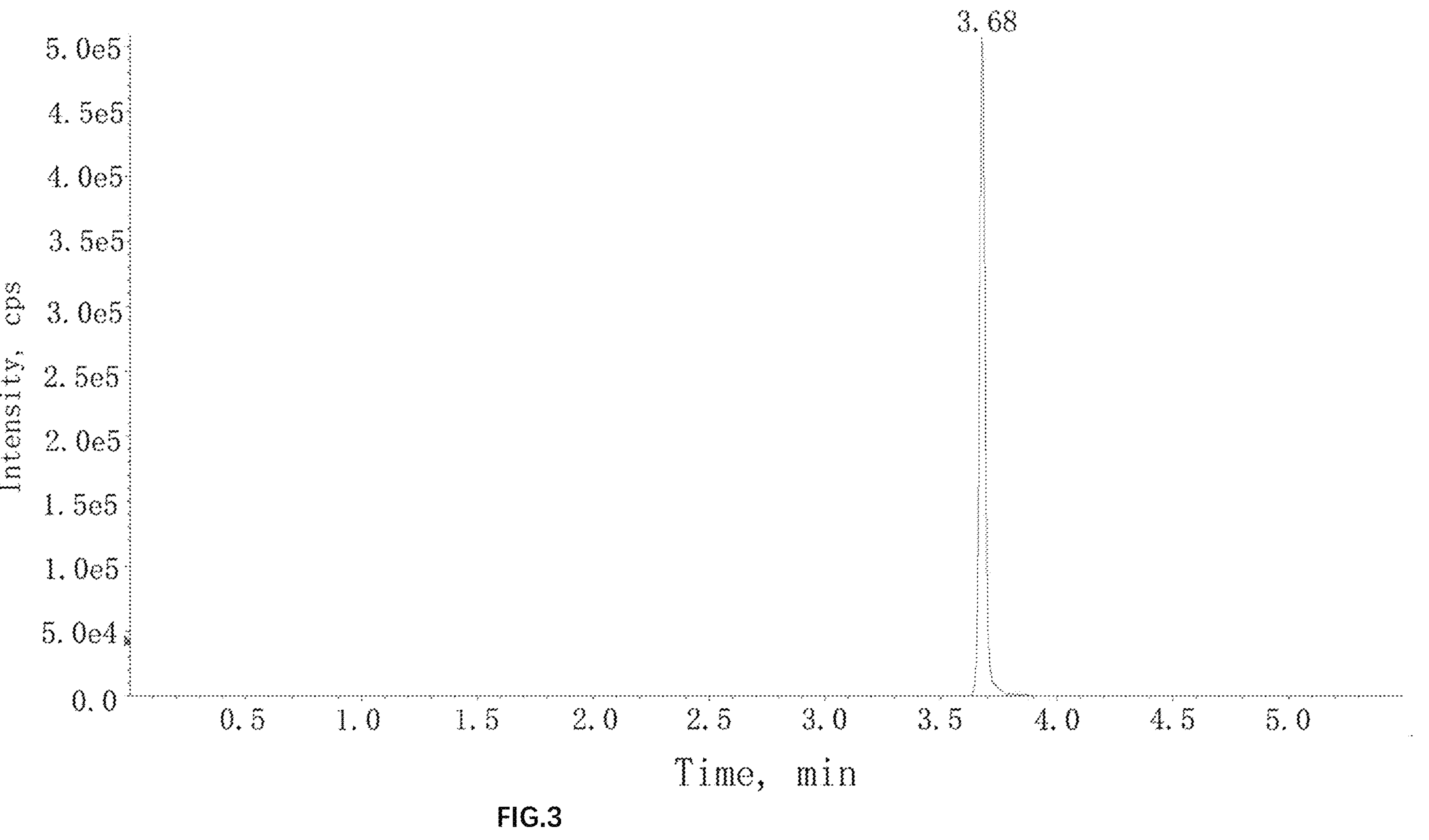
FIG. 3 shows detection chromatograms of duloxetine.
Figure 4:
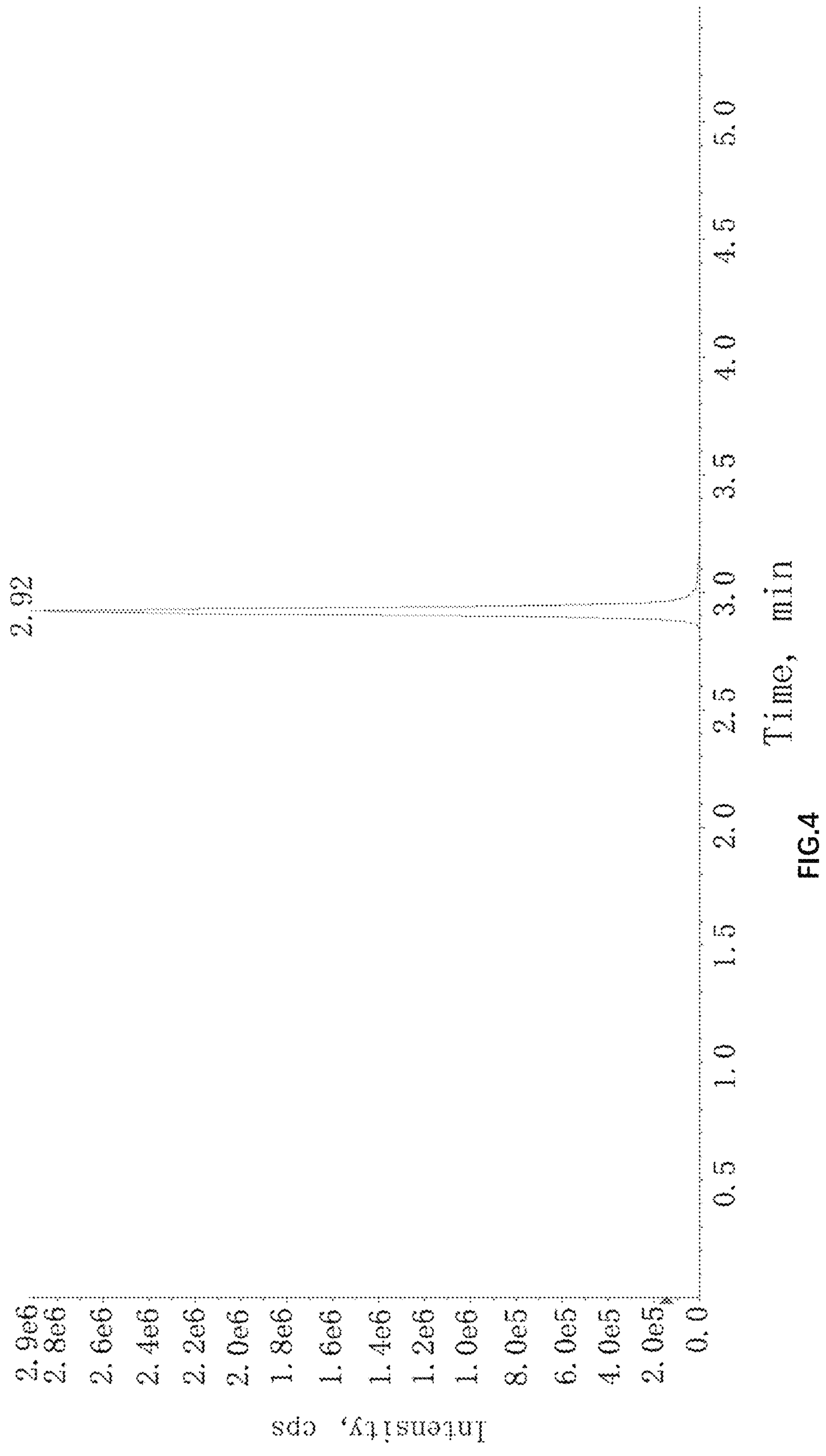
FIG. 4 shows detection chromatograms of imatinib.
Figure 5:
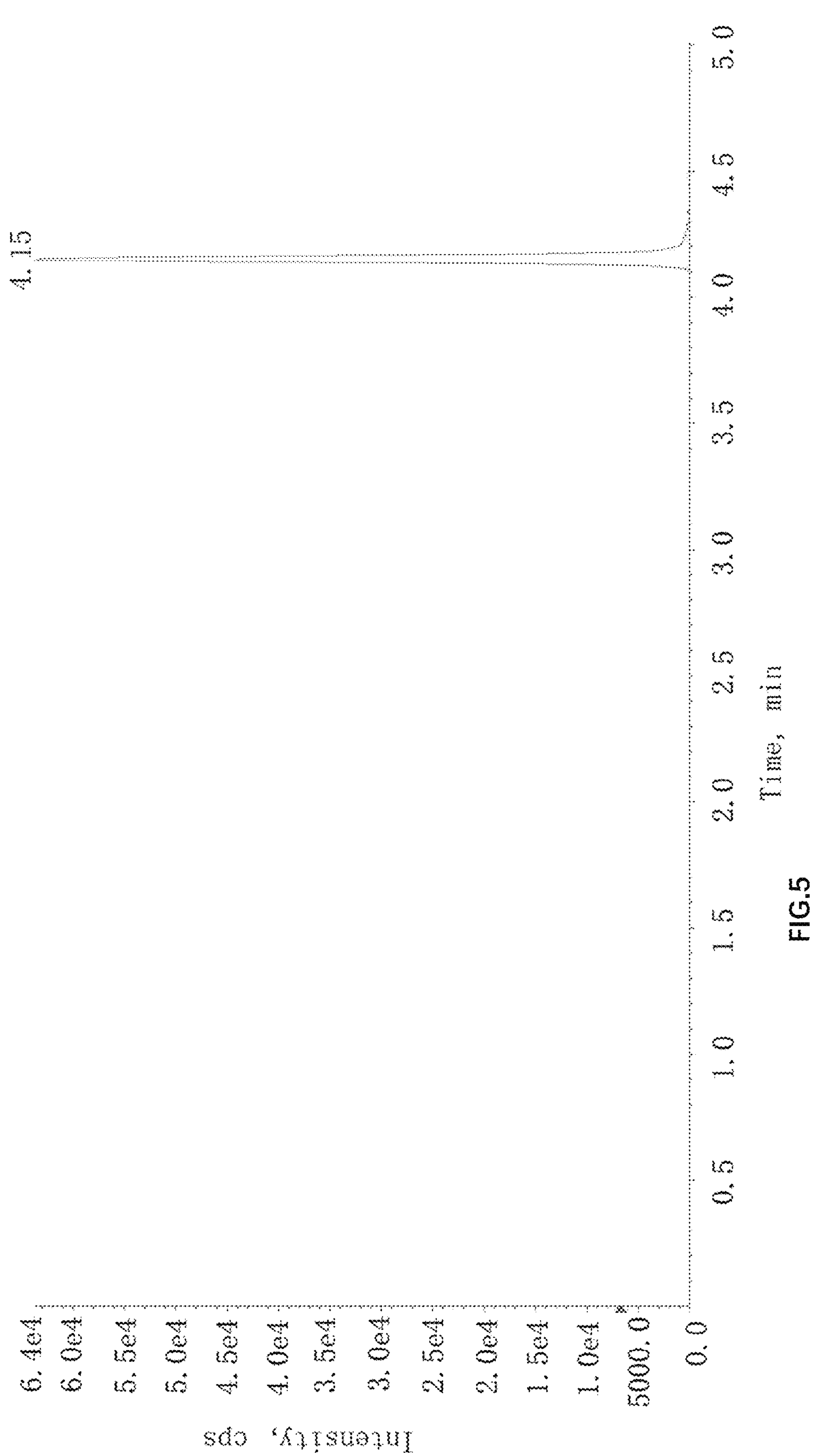
FIG. 5 shows detection chromatograms of lurasidone.
Figure 6:
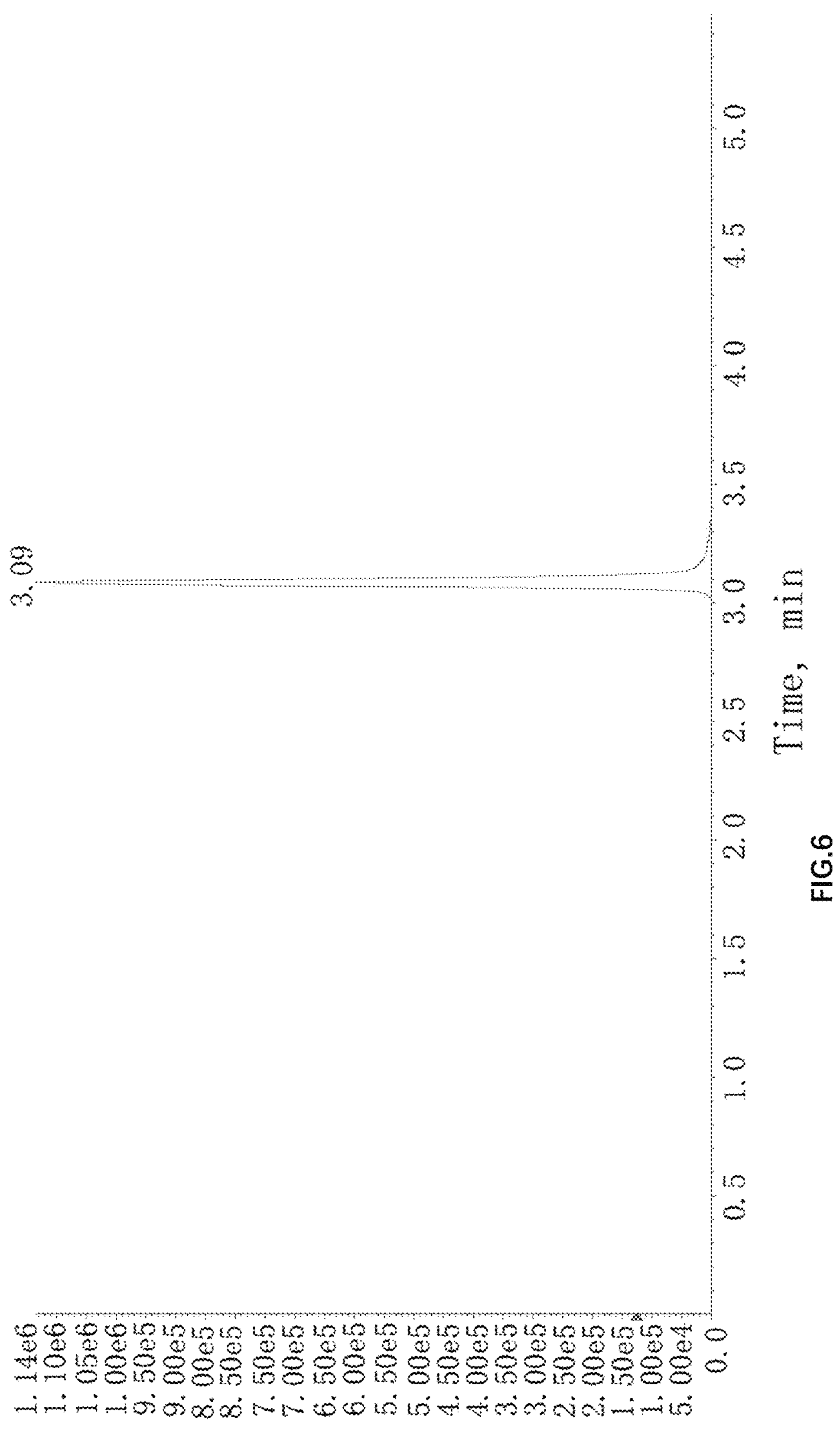
FIG. 6 shows detection chromatograms of osmertinib.
Figure 7:
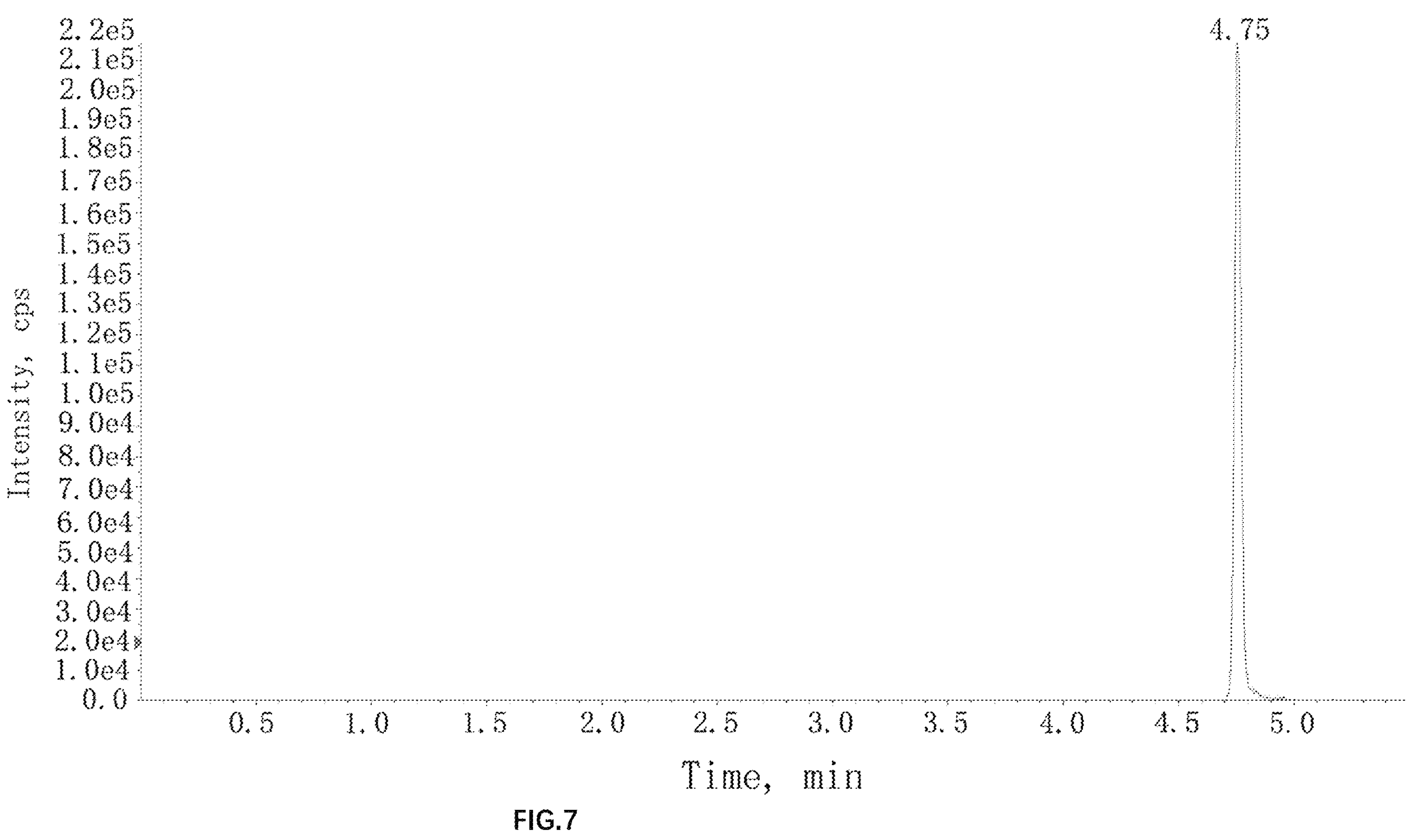
FIG. 7 shows detection chromatograms of paclitaxel.
Figure 8:
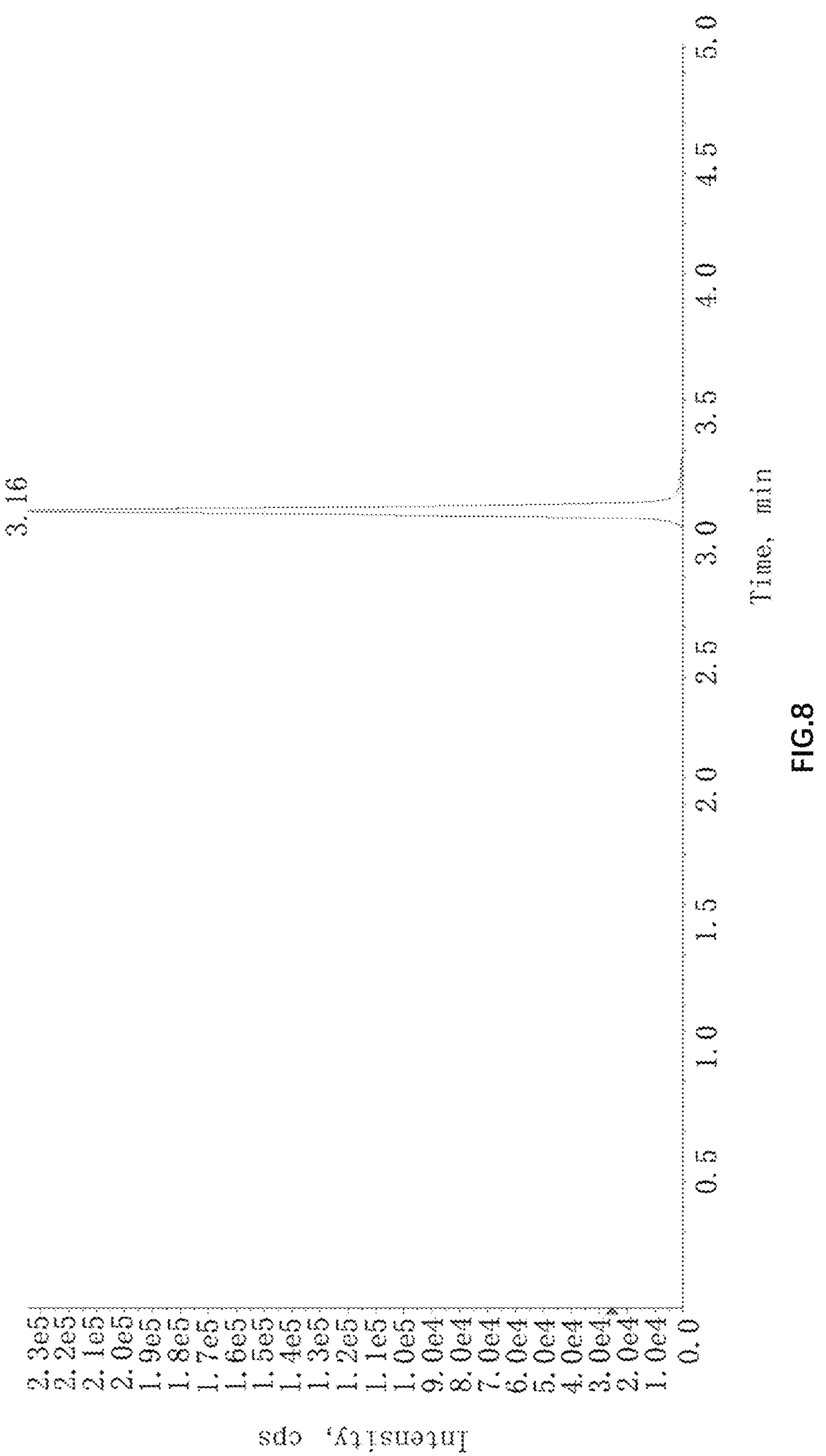
FIG. 8 shows detection chromatograms of quetiapine.
Figure 9:
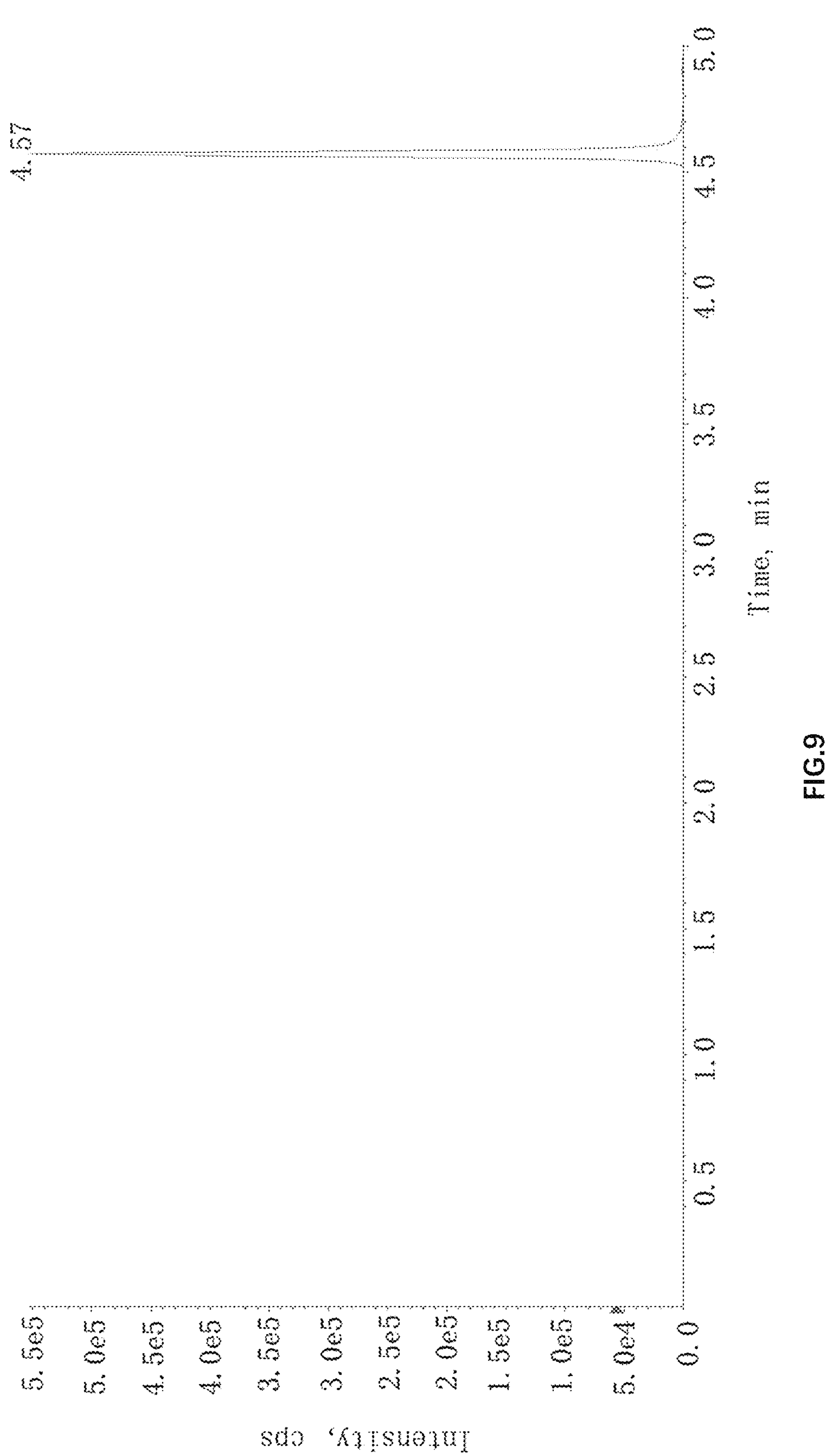
FIG. 9 shows detection chromatograms of stiripentol.
Figure 10:
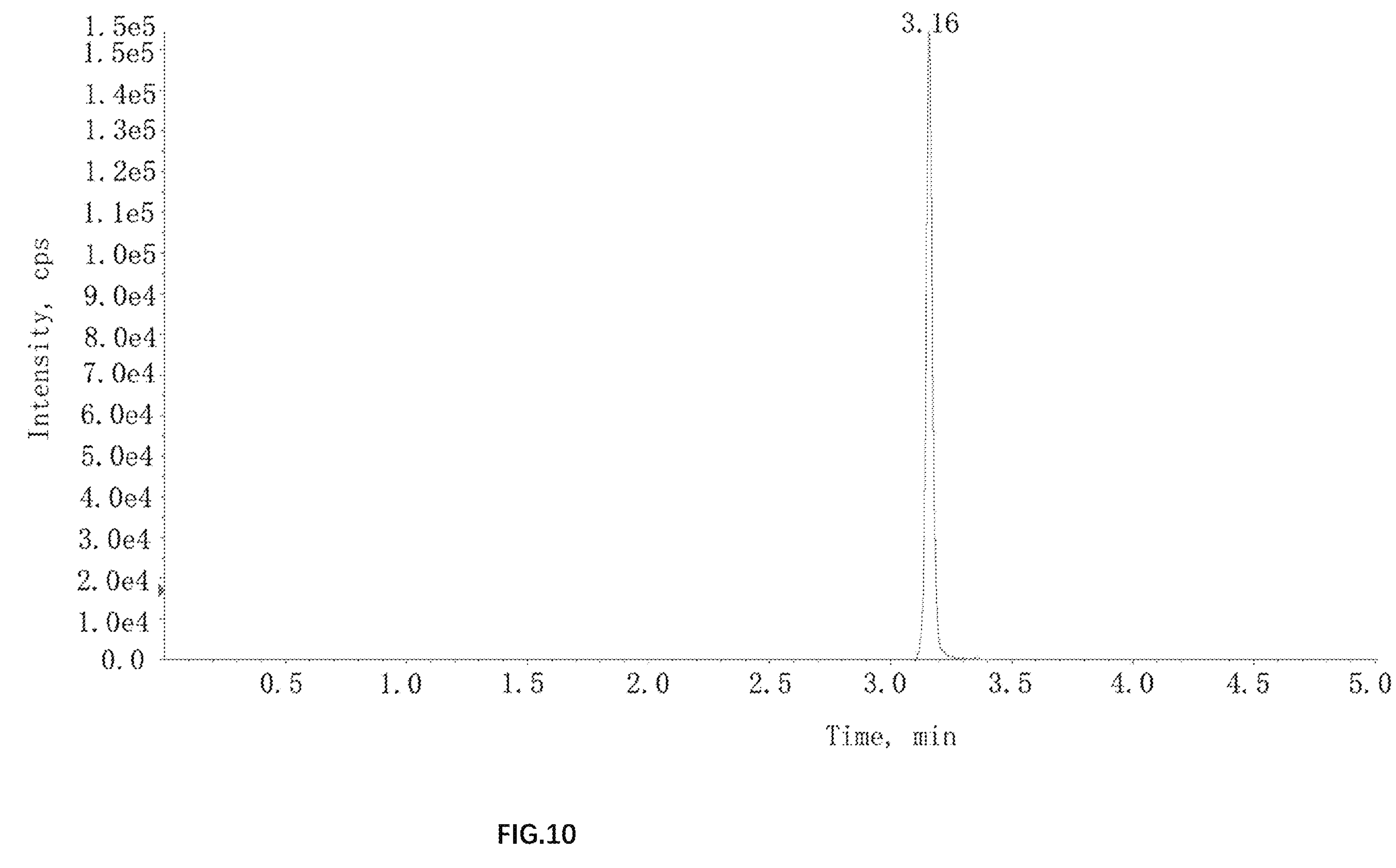
FIG. 10 shows detection chromatograms of ziprasidone.

The standard curve was established using the internal standard method. The validation records of the linear relationship are shown in Table 6, with the unit of measurement being ng/mL. Partial detection chromatograms are shown in FIGS. 1-4.

TABLE 6

| Standard Curve Information for Quantitative Detection of Drugs | | | | | |
|---|---|---|---|---|---|
| Drug Name | English Name | Linear Regression Equation (Correlation Coefficient r) (Weighting) | Linear Lower Limit | Linear Upper Limit | Concentration Unit |
| A Pu Zuo Lun | Alprazolam | y = 0.12979 x + 0.10886 (r = 0.99359)(weighting: 1/x^2) | 2.5 | 125 | ng/mL |
| Lv Xiao Xi Pan | Clonazepam | y = 0.13106 x + 0.04705 (r = 0.99877)(weighting: 1/x^2) | 2.5 | 125 | ng/ml |
| Mi Da Zuo Lun | Midazolam | y = 0.14256 x − 6.27431e−5 (r = 0.99520)(weighting: 1/x^2) | 2.5 | 125 | ng/mL |
| Lao La Xi Pan | Lorazepam | y = 0.16919 x − 0.03392 (r = 0.99724)(weighting: 1/x^2) | 10 | 500 | ng/ml |
| Zuo Pi Ke Long | Zopiclone | y = 0.48951 x + 0.03264 (r = 0.99847)(weighting: 1/x^2) | 10 | 500 | ng/ml |
| Ti Ma Xi Pan | Temazepam | y = 0.19743 x + 0.07999 (r = 0.99898)(weighting: 1/x^2) | 60 | 3000 | ng/mL |
| Xiu Xi Pan | Bromazepam | y = 0.25564 x + 0.04065 (r = 0.99670)(weighting: 1/x^2) | 12.5 | 625 | ng/ml |
| Xiao Xi Pan | Nitrazepam | y = 0.12557 x + 0.07990 (r = 0.99554)(weighting: 1/x^2) | 10 | 500 | ng/ml |

TABLE 6-continued

| Standard Curve Information for Quantitative Detection of Drugs | | | | | |
|---|---|---|---|---|---|
| Drug Name | English Name | Linear Regression Equation (Correlation Coefficient r) (Weighting) | Linear Lower Limit | Linear Upper Limit | Concent ration Unit |
| 6-Qiang Ding Luo Huan Tong | 6-Hydroxybuspirone | y = 0.19075 x + 0.06479 (r = 0.99433)(weighting: 1/x^2) | 0.75 | 37.5 | ng/ml |
| Ding Luo Huan Tong | Buspirone | y = 0.21287 x − 0.05871 (r = 0.99385)(weighting: 1/x^2) | 0.75 | 37.5 | ng/ml |
| Zha Lai Pu Long | Zaleplon | y = 0.11722 x −0.00151 (r = 0.99312)(weighting: 1 /x^2)) | 10 | 500 | ng/ml |
| Mei Jin Gang | Memantine | y = 0.24062 x + 0.04433 (r = 0.99892)(weighting: 1 /x^2) | 25 | 1250 | ng/ml |
| Duo Nai Pai Qi | Donepezil | y = 0.20483 x + 0.05813 (r = 0.99812)(weighting: 1/x^2) | 10 | 500 | ng/ml |
| Tan Du Luo Tong | Tandospirone | y = 0.15440 x + 0.01240 (r = 0.99756)(weighting: 1/x^2) | 0.5 | 25 | ng/ml |
| Di Xi Pan | Diazepam | y = 0.15588 x + 0.04256 (r = 0.99920)(weighting: 1/x^2) | 80 | 4000 | ng/ml |
| Qu Jia Di Xi Pan | Nordazepam | y = 0.19484 x + 0.14308 (r = 0.99143)(weighting: 1/x^2) | 80 | 4000 | ng/ml |
| Ao Sha Xi Pan | Oxazepam | y = 0.28252 x + 0.15902 (r = 0.99527)(weighting: 1/x^2) | 60 | 3000 | ng/mL |
| Zuo Bi Tan | Zolpidem | y = 0.30409 x + 0.05047 (r = 0.99962)(weighting: 1/x^2) | 12.5 | 625 | ng/ml |
| Ai Si Zuo Lun | Estazolam | y = 0.10539 x + 0.00569 (r = 0.99794)(weighting: 1/x^2) | 30 | 1500 | ng/ml |
| She Qu Lin | Sertraline | y = 1.51331 x + 0.36131 (r = 0.99702)(weighting: 1/x^2) | 4.5 | 450 | ng/ml |
| Fu Xi Ting | Fluoxetine | y = 0.19494 x + 0.12129 (r = 0.99377)(weighting: 1/x^2) | 10 | 1000 | ng/ml |
| Qu Jia Fu Xi Ting | Norfluoxetine | y = 0.35178 x + 0.17339 (r = 0.99789)(weighting: 1/x^2) | 12 | 1200 | ng/ml |
| Ai Si Xi Tai Pu Lan | Escitalopram | y = 0.41512 x + 0.09433 (r = 0.99935)(weighting: 1/x^2) | 5 | 500 | ng/ml |
| Fu Fu Sha Ming | Fluvoxamine | y = 0.28307 x + 0.14526 (r = 0.99208)(weighting: 1/x^2) | 10 | 1000 | ng/mL |
| Pa Luo Xi Ting | Paroxetine | y = 0.65620 x + 0.14260 (r = 0.99712)(weighting: 1/x^2) | 6 | 600 | ng/ml |
| Wen La Fa Xin | Venlafaxine | y = 0.42472 x + 0.00405 (r = 0.99635)(weighting: 1/x^2) | 8 | 800 | ng/ml |
| O-Qu Jia Wen La Fa Xin | O-Demethyl-Venlafaxine | y = 0.55527 x + 0.15963 (r = 0.99363)(weighting: 1/x^2) | 10 | 1000 | ng/mL |
| Du Luo Xi Ting | Duloxetine | y = 0.41569 x + 0.05542 (r = 0.99653)(weighting: 1/x^2) | 5 | 500 | ng/ml |
| Mi Dan Ping | Mirtazapine | y = 0.12474 x + 0.03833 (r = 0.99831)(weighting: 1/x^2) | 3 | 300 | ng/ml |
| Qu Zuo Tong | Trazodone | y = 0.55302 x + 0.04660 (r = 0.99954)(weighting: 1/x^2) | 40 | 4000 | ng/mL |
| Mi Na Pu Lun | Milnacipran | y = 0.07909 x + −0.01527 (r = 0.99792)(weighting: 1/x^2) | 6 | 600 | ng/ml |
| A Mi Ti Lin | Amitriptyline | y = 0.50580 x + 0.17804 (r = 0.99850)(weighting: 1/x^2) | 6 | 600 | ng/mL |
| Qu Jia Ti Lin | Nortriptyline | y = 0.02916 x + 0.01207 (r = 0.99896)(weighting: 1/x^2) | 6 | 600 | ng/ml |
| Duo Sai Ping | Doxepin | y = 0.51942 x + 0.08507 (r = 0.99741)(weighting: 1/x^2) | 5 | 500 | ng/ml |
| Fu Liu Xi Ting | Vortioxetine | y = 0.99614 x + 0.29055 (r = 0.99720)(weighting: 1/x^2) | 2 | 200 | ng/mL |
| Qu Jia Lv Mi Pa Ming | Norclomipramine | y = 0.41671 x + 0.12435 (r = 0.99876)(weighting: 1/x^2) | 10 | 1000 | ng/ml |
| Lv Mi Pa Ming | Clomipramine | y = 0.33783 x + 0.25470 (r = 0.99867)(weighting: 1/x^2) | 10 | 1000 | ng/ml |
| A Ge Mei La Ting | Agomelatine | y = 1.15071 x + 0.27630 (r = 0.99424)(weighting: 1/x^2) | 5 | 750 | ng/mL |
| An Fei Ta Tong | Bupropion | y = 0.02105 x + 0.00152 (r = 0.99915)(weighting: 1/x^2) | 5 | 500 | ng/ml |
| Mi An Se Lin | Mianserine | y = 0.71437 x + 0.05935 (r = 0.99856)(weighting: 1/x^2) | 3 | 300 | ng/ml |
| Qu Jia Duo Sai Ping | Nordexepin | y = 0.34234 x + 0.08923 (r = 0.99906)(weighting: 1/x^2) | 5 | 500 | ng/mL |
| Qiang An Fei Ta Tong | Hydroxybupropion | y = 0.68427 x + 0.04917 (r = 0.99890)(weighting: 1/x^2) | 40 | 4000 | ng/ml |
| Ao Dan Ping | Olanzapine | y = 0.14105 x + −0.02491 (r = 0.99419)(weighting: 1/x^2) | 3 | 300 | ng/ml |
| Lv Dan Ping | Clozapine | y = 0.02208 x + 0.00738 (r = 0.99554)(weighting: 1/x^2) | 25 | 2500 | ng/ml |
| Pa Pan Li Tong | Paliperidone | y = 0.04397 x + 0.00290 (r = 0.99940)(weighting: 1/x^2) | 2 | 200 | ng/ml |

TABLE 6-continued

Standard Curve Information for Quantitative Detection of Drugs

| Drug Name | English Name | Linear Regression Equation (Correlation Coefficient r) (Weighting) | Linear Lower Limit | Linear Upper Limit | Concent ration Unit |
|---|---|---|---|---|---|
| Li Pei Tong | Risperidone | y = 0.08467 x + 0.01762 (r = 0.99600)(weighting: 1/x^2) | 1.5 | 150 | ng/ml |
| Tuo Qing A Li Pai Zuo | Dehydro-Aripiprazole | y = 0.13925 x + 0.01720 (r = 0.99857)(weighting: 1/x^2) | 7 | 700 | ng/ml |
| A Li Pai Zuo | Aripiprazole | y = 0.13096 x + 0.01552 (r = 0.99714)(weighting: 1/x^2) | 15 | 1500 | ng/ml |
| An Huang Bi Li | Amisulpride | y = 0.02387 x + 0.00665 (r = 0.99810) (weighting: 1/x^2) | 20 | 2000 | ng/mL |
| Kui Liu Ping | Quetiapine | y = 0.03244 x + 0.01044 (r = 0.99741) (weighting: 1 /x^2) | 20 | 2000 | ng/mL |
| Lv Bing Qin | Chlorpromazine | y = 0.07473 x + 0.02948 (r = 0.99559) (weighting: 1/x^2) | 9 | 900 | ng/mL |
| Qi La Xi Tong | Ziprasidone | y = 0.09283 x + 0.02038 (r = 0.99584) (weighting: 1/x^2) | 8 | 800 | ng/ml |
| N-Qu Jia Lv Dan Ping | Norclozapine | y = 0.05125 x + 0.04969 (r = 0.99732) (weighting: 1/x^2) | 10 | 1000 | ng/ml |
| Lv Pai Ding Chun | Haloperidol | y = 0.06629 x + 0.01283 (r = 0.99610) (weighting: 1/x^2) | 0.3 | 30 | ng/mL |
| Fen Nai Jing | Perphenazine | y = 0.01940 x + 0.01813 (r = 0.99447) (weighting: 1/x^2) | 0.3 | 30 | ng/ml |
| Shu Bi Li | Sulpiride | y = 0.01767 x + 0.00530 (r = 0.99794) (weighting: 1/x^2) | 24 | 2400 | ng/ml |
| Qu Jia Kui Liu Ping | Norquetiapine | y = 0.05977 x + 0.02183 (r = 0.99822) (weighting: 1/x^2) | 10 | 1000 | ng/ml |
| Fu Fen Nai Jing | Fluphenazine | y = 0.04040 x + 0.02520 (r = 0.99492) (weighting: 1/x^2) | 0.3 | 30 | ng/ml |
| Liu Li Da Qin | Thioridazine | y = 0.06611 x + 0.02198 (r = 0.99921) (weighting: 1/x^2) | 9 | 900 | ng/mL |
| Tuo Mo Xi Ting | Tomoxetine | y = 0.15532 x + 0.09227 (r = 0.99642) (weighting: 1/x^2) | 36 | 3600 | ng/ml |
| Lu La Xi Tong | Lurasidone | y = 0.06007 x + 0.00331 (r = 0.99575) (weighting: 1/x^2) | 1.8 | 180 | ng/ml |
| Bu Nan Se Lin | Blonaserin | y = 0.02357 x + 6.80457e−4 (r = 0.99683)(weighting: 1/ x^2) | 0.12 | 12 | ng/ml |
| Ma Pu Ti Lin | Maprotiline | y = 0.38557 x − 0.00133 (r = 0.99690) (weighting: 1/x^2) | 5 | 500 | ng/mL |
| Pai Jia Zhi | Methylphenidate | y = 0.08954 x + 0.01651 (r = 0.99776) (weighting: 1/x^2) | 1 | 100 | ng/ml |
| Ka Ba La Ting | Rivastigmine | y = 0.04227 x − 8.32040e−5 (r = 0.99825)(weighting: 1/ x^2) | 1 | 100 | ng/ml |
| Pai Luo Pi Long | Perospirone | y = 0.05807 x + 0.10564 (r = 0.99454) (weighting: 1/x^2) | 0.2 | 20 | ng/mL |
| Qu Jia Ao Dan Ping | NorOlanzapine | y = 0.07637 x − 0.04104 (r = 0.99514) (weighting: 1/x^2) | 1 | 100 | ng/mL |
| Ka Ma Xi Ping Huan Yang Hua Wu | Carbamazepine-10,11-epoxide | y = 0.13736 x + 0.06484 (r = 0.99907) (weighting: 1/x^2) | 100 | 10000 | ng/ml |
| Qu Jia She Qu Lin | NorSertraline | y = 0.54843 x + 0.02690 (r = 0.99705) (weighting: 1/x^2) | 12 | 1200 | ng/mL |
| Qu Jia Xi Tai Pu Lan | NorCitalopram | y = 0.17819 x + 0.04723 (r = 0.99480) (weighting: 1/x^2) | 2.5 | 250 | ng/mL |
| Qu Jia Mi Dan Ping | NorMirtazapine | y = 0.66691 x + 0.91053 (r = 0.99450) (weighting: 1/x^2) | 3 | 300 | ng/ml |
| Huan Yang Xian An | Cyclophosphamide | y = 0.42743 x − 0.12013 (r = 0.99544) (weighting: 1/x^2) | 200 | 40000 | ng/ml |
| Yi Huan Lin Xian An | Ifosfamide | y = 6.11662e4 x + 6002.7742 (r = 0.99945)(weighting: 1/x^2) | 200 | 40000 | ng/ml |
| Jia An Die Ling | Methotrexate | y = 0.10278 x + 0.05731 (r = 0.99709) (weighting: 1/x^2) | 40 | 8000 | ng/ml |
| Ka Pei Ta Bin | Capecitabine | y = 0.03727 x − 0.00180 (r = 0.99676) (weighting: 1/x^2) | 30 | 6000 | ng/ml |
| Yi Li Ti Kang | Irinotecan | y = 0.07295 x + 0.02749 (r = 0.99292) (weighting: 1/x^2) | 40 | 8000 | ng/mL |
| Zi Shan Chun | Paclitaxel | y = 0.15234 x + 0.03796 (r = 0.99597) (weighting: 1/x^2) | 40 | 8000 | ng/ml |
| Duo Xi Ta Sai | Docetaxel | y = 0.07349 x + 0.02274 (r = 0.99258) (weighting: 1/x^2) | 40 | 8000 | ng/ml |
| A Fa Ti Ni | Afatinib | y = 0.00158 x + 1.30776e−4 (r = 0.99499)(weighting: 1/x^2) | 8 | 800 | ng/ml |
| A Pa Ti Ni | Rivoceranib | y = 0.03383 x + 0.02787 (r = 0.99367) (weighting: 1/x^2) | 80 | 8000 | ng/ml |

TABLE 6-continued

Standard Curve Information for Quantitative Detection of Drugs

| Drug Name | English Name | Linear Regression Equation (Correlation Coefficient r) (Weighting) | Linear Lower Limit | Linear Upper Limit | Concent ration Unit |
|---|---|---|---|---|---|
| Ai Ke Ti Ni | Icotinib | y = 0.01659 x + 0.00556 (r = 0.99712) (weighting: 1/x^2) | 100 | 10000 | ng/ml |
| E Luo Ti Ni | Erlotinib | y = 0.03082 x + 0.00810 (r = 0.99861) (weighting: 1/x^2) | 80 | 8000 | ng/ml |
| Ji Fei Ti Ni | Gefitinib | y = 0.03107 x + 0.01514 (r = 0.99905) (weighting: 1/x^2) | 40 | 4000 | ng/ml |
| Ke Zuo Ti Ni | Crizotinib | y = 0.05616 x + 0.01223 (r = 0.99706) (weighting: 1/x^2) | 40 | 4000 | ng/ml |
| Rui Ge Fei Ni | Regorafenib | y = 0.06561 x + 0.02210 (r = 0.99801) (weighting: 1/x^2) | 200 | 20000 | ng/ml |
| Wei Mo Fei Ni | Vemurafenib | y = 0.30460 x + 0.07434 (r = 0.99798) (weighting: 1/x^2) | 2.5 | 250 | ug/mL |
| Yi Ma Ti Ni | Imatinib | y = 0.07579 x + 0.02734 (r = 0.99795) (weighting: 1/x^2) | 100 | 10000 | ng/ml |
| N-Qu Jia Yi Ma Ti Ni | N-Desmethylimatinib | y = 0.08801 x − 6.76912e−4 (r = 0.99737) (weighting: 1/x^2) | 50 | 5000 | ng/mL |
| A Lai Ti Ni | Alectinib | y = 0.03011 x − 0.00545 (r = 0.99579) (weighting: 1/x^2) | 80 | 8000 | ng/ml |
| Ao Xi Ti Ni | Osimertinib | y = 0.06288 x + 0.00792 (r = 0.99741) (weighting: 1/x^2) | 50 | 5000 | ng/ml |
| Mei Tuo Luo Er | Metoprolol | y = 0.00246 x + −0.00314 (r = 0.99614)(weighting: 1/x^2) | 0.5 | 500 | ng/ml |
| Bi Suo Luo Er | Bisoprolol | y = 5868.40833 x + 462.38218 (r = 0.99893)(weighting:1/x^2) | 1 | 1000 | ng/ml |
| Xiao Ben Di Ping | Nifedipine | y = 0.00223 x + 3.92926e−4 (r = 0.99879)(weighting: 1/x^2) | 0.5 | 500 | ng/ml |
| An Lv Di Ping | Amlodipine | y = 0.04502 x + −0.03815 (r = 0.99259) (weighting: 1 /x^2) | 0.1 | 100 | ng/ml |
| A Tuo Fa Ta Ting Gai | Aorvastatin | y = 436.78822 x + 285.95536 (r = 0.99944)(weighting: 1/x^2) | 0.25 | 250 | ng/mL |
| 2-Qiang Ji A Tuo Fa Ta Ting | Ortho-Hydroxyatorvastatin | y = 0.00412 x − 7.9696e−4 (r = 0.99776)(weighting: 1/x^2) | 0.25 | 250 | ng/ml |
| Rui Shu Fa Ta Ting | Losartan | y = 0.947302 + 1.10104e−4 (r = 0.99927)(weighting: 1/x^2) | 0.4 | 400 | ng/mL |
| Lv Sha Tan | Rosuvastatin | y = 0.969678 x − 4.07242e−4 (r = 0.99666)(weighting:1/x^2) | 5 | 5000 | ng/mL |
| Lv Sha Tan Dai Xie Wu | losartan-metabolite | y = 1.09628 x − 1940.56631 (r = 0.99752)(weighting: 1/x^2) | 6 | 6000 | ng/mL |
| Xie Sha Tan | Valsartan | y = 5.14662e4 x − 304.91300 (r = 0.99638)(weighting: 1/x^2) | 50 | 50000 | ng/ml |
| Er Bei Sha Tan | irbesartan | y = 7.05027e4 x − 1164.4660(r = 0.99908)(weighting: 1/ x^2) | 25 | 25000 | ng/mL |
| Ti Mi Sha Tan | Telmisartan | y = 0.00991 x − 6.68784e−5 (r = 0.99860)(weighting: 1/x^2) | 15 | 15000 | ng/mL |
| Lv Bi Ge Lei Dai Xie Wu | Clopidogrel-metabolite | y = 22440.12x − 2709.62865 (r = 0.99926)(weighting: 1/ x^2) | 20 | 20000 | ng/ml |
| Shui Yang Suan | Salicylic acid | y = 8.26077 x + 2.36163 (r = 0.99119) (weighting: 1/x^2) | 125 | 125000 | ng/ml |
| Ti Ge Rui Luo | Ticagrelor | y = 10195.9924 x + 777.9283 (r = 0.9979)(weighting: 1/ x^2) | 20 | 20000 | ng/ml |
| Ti Ge Rui Luo Dai Xie Wu M8 | Ticagrelor-metabolite M8 | y = 6858.8468 x − 103.48619 (r = 0.9962)(weighting: 1/ x^2) | 20 | 20000 | ng/mL |
| La Mo San Qin | Lamotrigine | y = 0.33246 x + 0.07829 (r = 0.99945) (weighting: 1/ x^2) | 0.3 | 30 | ug/mL |
| 10-Qiang Ji Ka Ma Xi Ping | 10-OH Car | y = 0.18606 x + 0.10384 (r = 0.99927) (weighting: 1/x^2) | 0.8 | 80 | ug/mL |
| Ka Ma Xi Ping | Carbamazepine | y = 0.81862 x − 0.09196 (r = 0.99519) (weighting: 1/x^2) | 0.3 | 30 | ug/mL |
| Ben Tuo Ying Na | Phenytoin Sodium | y = 0.08617 x + 0.00179 (r = 0.99454) (weighting: 1/x^2) | 0.8 | 80 | ug/mL |
| Tuo Bi Zhi | Topiramate | y = 0.12119 x + 0.00869 (r = 0.99503) (weighting: 1/x^2) | 0.3 | 30 | ug/mL |
| Pu Li Mi Tong | Primidone | y = 0.51225 x + 0.04547 (r = 0.99915) (weighting: 1/x^2) | 0.4 | 40 | ug/mL |
| Lu Fei Xian An | Rufinamide | y = 0.98017 x + 0.20331 (r = 0.99892) (weighting: 1/x^2) | 0.8 | 80 | ug/mL |
| Si Ti Wu Chun | Striripentol | y = 0.13652 x + 0.04120 (r = 0.99773) (weighting: 1/x^2) | 0.3 | 30 | ug/mL |
| Bi Lun Pa Nai | Perampanel | y = 0.18118 x + 0.05423 (r = 0.99837) (weighting: 1/x^2) | 0.032 | 1.6 | ug/mL |
| Zuo Ni Sha An | Zonisamide | y = 0.75376 x + 0.24621 (r = 0.99973) (weighting: 1/x^2) | 1 | 100 | ug/mL |
| La Kao Sha An | Lacosamide | y = 0.24702 x + 0.04437 (r = 0.99934) (weighting: 1/x^2) | 0.3 | 30 | ug/mL |

TABLE 6-continued

| Standard Curve Information for Quantitative Detection of Drugs | | | | | |
|---|---|---|---|---|---|
| Drug Name | English Name | Linear Regression Equation (Correlation Coefficient r) (Weighting) | Linear Lower Limit | Linear Upper Limit | Concent ration Unit |
| Bing Wu Suan | Valproic Acid | y = 0.09191 x + 0.02014 (r = 0.99675) (weighting: 1/x^2) | 2.5 | 250 | ug/mL |
| Ben Ba Bi Tuo | Phenobarbital | y = 0.16275 x + 0.04639 (r = 0.99665) (weighting: 1/x^2) | 1.6 | 80 | ug/mL |
| Duo Nai Pai Qi | Donepezil | y = 1.0028 x − 0.0914 (r = 0.99987) (weighting: 1/x^2) | 0.003 | 0.3 | ug/mL |
| Mei Jin Gang | Memantine | y = 1.0228 x − 0.0991 (r = 0.99724) (weighting: 1/x^2) | 0.007 | 0.7 | ug/mL |
| Jia Ba Pen Ding | Gabapentin | y = 0.98114 x + 0.29262 (r = 0.99998) (weighting: 1/x^2) | 0.5 | 50 | ug/mL |
| Pu Rui Ba Lin | Pregabalin | y = 0.93551 x + 2.53063 (r = 0.99987) (weighting: 1/x^2) | 0.2 | 20 | ug/mL |
| Zuo Yi La Xi Tan | Levetiracetam | y = 1.0023 x − 0.79774 (r = 0.99995) (weighting: 1/x^2) | 1 | 100 | ug/mL |
| Ao Ka Xi Ping | Oxcarbazepine | y = 0.57466 x + 0.50228 (r = 0.99507) (weighting: 1/x^2) | 0.15 | 15 | ug/mL |
| Mo Xi Sha Xing | Moxifloxacin | y = 0.02636 x + −5.91367e−4 (r =0.99830) (weighting: 1/x^2) | 0.16 | 8 | ug/mL |
| Wan Gu Mei Su | Vancomycin | y = 0.13897 x + 0.07571 (r = 0.99800) (weighting: 1/x^2) | 0.8 | 40 | ug/mL |
| Ti Jia Huan Su | Tigecycline | y = 0.00382 x + 0.00111 (r = 0.99407) (weighting: 1/x^2) | 0.05 | 2.5 | ug/mL |
| Qu Jia Wan Gu Mei Su | Norvancomycin | y = 0.11850 x + 0.03284 (r = 0.99383) (weighting: 1/x^2) | 1 | 50 | ug/mL |
| Duo Nian Jun Su B | Polymyxin B1 | y = 0.02241 x + 0.00354 (r = 0.99657) (weighting: 1/x^2) | 1 | 50 | ug/mL |
| Li Nai Zuo An | Linezolid | y = 0.13325 x + 0.01996 (r = 0.99910) (weighting: 1/x^2) | 0.6 | 30 | ug/mL |
| Huang An Jia E Zuo | Sufamethoxazole | y = 0.08346 x + 0.02922 (r = 0.99897) (weighting: 1/x^2) | 5 | 250 | ug/mL |
| Zuo Yang Fu Sha Xing | Levofloxacin | y = 0.03485 x + 0.00989 (r = 0.99425) (weighting: 1/x^2) | 0.4 | 20 | ug/mL |
| Duo Nian Jun Su B2 | Polymyxin B2 | y = 0.00398 x + 0.01073 (r = 0.99669) (weighting: 1/x^2) | 0.2 | 10 | ug/mL |
| Huan Bing Sha Xing | Ciprofloxacin | y = 0.23337 x + 0.11105 (r = 0.99944) (weighting: 1/x^2) | 0.4 | 20 | ug/mL |
| Tou Bao Bi Wo | Cefepime | y = 0.9405x + 8.0751 (r = 0.99824) (weighting: 1/x^2) | 0.8 | 40 | ug/mL |
| Mei Luo Pei Nan | Meropenem | y = 0.9322x + 8.3563 (r = 0.99981) (weighting: 1/x^2) | 1 | 50 | ug/mL |
| Tou Bao Pai Tong | Cefperazone | y = 0.9994x + 0.2536 (r = 0.99648) (weighting: 1/x^2) | 5 | 250 | ug/mL |
| Pai La Xi Lin | Piperacillin | y = 1.0011x + 0.0385 (r = 0.99576) (weighting: 1/x^2) | 4 | 200 | ug/mL |
| A Mo Xi Lin | Amoxicillin | y = 1.0286x − 1.9675 (r = 0.99698) (weighting: 1/x^2) | 1 | 50 | ug/mL |
| Ta Zuo Ba Tan | Tazuobactam | y = 0.9824x + 2.3448 (r = 0.99843) (weighting: 1/x^2) | 1 | 50 | ug/mL |
| Ya An Pei Nan | Imipenem | y = 0.9892x + 1.5094 (r = 0.99904) (weighting: 1/x^2) | 0.4 | 20 | ug/mL |
| Fen Tai Ni | Fentanyl | y = 0.9519x + 6.1458 (r = 0.99999) (weighting: 1/x^2) | 0.3 | 300 | ng/ml |
| Ma Fei | Morphine | y = 1.0931x − 7.6192 (r = 0.99327) (weighting: 1/x^2) | 1 | 1000 | ng/ml |
| Qiang Kao Tong | Oxycodone | y = 0.9934x + 11.744 (r = 0.99815) (weighting: 1/x^2) | 1 | 1000 | ng/ml |
| 5-Fu Niao Mi Ding | 5-Fluorouracil | y = 0.9224x + 9.8006 (r = 0.99776) (weighting: 1 /x^2) | 50 | 10000 | ng/ml |
| Bi Suo Luo Er | Bisoprolol | y = 0.9545x + 25.451 (r = 0.99964) (weighting: 1/x^2) | 0.05 | 5 | ng/ml |
| Yin Da Pa An | Indapamide | y = 0.9523x + 26.308 (r = 0.99976) (weighting: 1/x^2) | 0.2 | 20 | ng/ml |
| Ni Mo Di Ping | Nimodipine | y = 1.0297x − 28.066 (r = 0.99821) (weighting: 1/x^2) | 0.05 | 5 | ng/ml |
| Yi Na Pu Li | Enalapril | y = 0.9796x + 0.3332 (r = 0.99903) (weighting: 1/x^2) | 0.0025 | 0.25 | ng/mL |
| Pei Duo Pu Li | Perindopril | y = 0.999x − 0.0726 (r = 0.99879) (weighting: 1/x^2) | 0.2 | 20 | ng/ml |
| Pu Nai Nuo Er | Propranolol | y = 1.1122x − 0.4781 (r = 0.99853) (weighting: 1/x^2) | 0.2 | 20 | ng/ml |
| Fu Xin Pu Li | Fosinopril | y = 1.0055x − 1.6484 (r = 0.99828) (weighting: 1/x^2) | 0.5 | 50 | ng/ml |
| Ka Tuo Pu Li Er Liu Hua Wu | Captopril-dis | y = 0.9856x + 19.549 (r = 0.99877) (weighting: 1/x^2) | 0.2 | 20 | ng/ml |

TABLE 6-continued

Standard Curve Information for Quantitative Detection of Drugs

| Drug Name | English Name | Linear Regression Equation (Correlation Coefficient r) (Weighting) | Linear Lower Limit | Linear Upper Limit | Concent ration Unit |
|---|---|---|---|---|---|
| Ti Mi Sha Tan | Telmisartan | y = 0.9711x + 24.904 (r = 0.99886) (weighting: 1/x^2) | 0.005 | 0.5 | ng/mL |
| Mei Tuo Luo Er | Metoprolol | y = 0.9969x − 0.1431 (r = 0.99837) (weighting: 1/x^2) | 0.05 | 5 | ng/ml |
| Lv Sha Tan | Losartan | y = 0.9952x + 0.3035 (r = 0.99912) (weighting: 1/x^2) | 1 | 100 | ng/ml |
| Lv Sha Tan Suo Suan | Losartan-Meta | y = 0.9548x + 158.56 (r = 0.99904) (weighting: 1/x^2) | 0.2 | 20 | ng/mL |
| Er Bei Sha Tan | Irbesartan | y = 1.1075x − 0.8726 (r = 0.99834) (weighting: 1/x^2) | 1 | 100 | ng/ml |
| Xie Sha Tan | Valsartan | y = 1.0662x − 0.6218 (r = 0.99721) (weighting: 1/x^2) | 0.05 | 5 | ng/ml |
| 4-Xie Sha Tan | Valsartan-Meta | y = 1.8319x − 1.936 (r = 0.99901) (weighting: 1/x^2) | 0.0025 | 0.25 | ng/ml |
| An Lv Di Ping | Amlodipine | y = 0.9132x + 10.581(r = 0.99875) (weighting: 1/x^2) | 0.005 | 0.5 | ng/ml |
| Tuo Qing Fei Luo Di Ping | Felodipine Meta | y = 0.9971x + 1.6397(r = 0.99961) (weighting: 1/x^2) | 0.005 | 0.5 | ng/mL |
| Kan Li Tong | Spironolactone-Meta | y = 0.9627x + 4.996(r = 0.99949) (weighting: 1/x^2) | 1 | 100 | ng/mL |
| Ka Tuo Pu Li | Captopril | y = 0.9371x + 0.5829(r = 0.99478) (weighting: 1/x^2) | 0.2 | 20 | ng/ml |

The standard curve was prepared using a human-like serum matrix and treated simultaneously with the samples to be detected for detection. The summary of detection information for non-quantitative screening drugs is shown in Table 7.

TABLE 7

Summary of Detection Information for Non-quantitative Screening Drugs

| No. | Chinese Name | English Name | Drug Category | Q1 | Q3 |
|---|---|---|---|---|---|
| 1 | Yi Xian Jia An Lin | Acephate | Pesticide | 184 | 143 |
| 2 | Ding Chong Mi | Acetamiprid | Pesticide | 223 | 126 |
| 3 | Yi Cao An | Acetochlor | Pesticide | 270.2 | 148.2 |
| 4 | Jia Cao An | Alachlor | Pesticide | 270.1 | 238.1 |
| 5 | Ti Mie Wei | Aldicarb | Pesticide | 208 | 116 |
| 6 | Ti Mie Wei Feng | Aldicarb Sulfone | Pesticide | 223 | 86 |
| 7 | Ti Mie Wei Ya Feng | Aldicarb-sulfoxide | Pesticide | 207 | 89 |
| 8 | You Mie Jing | Ametryn | Pesticide | 228.1 | 186.2 |
| 9 | Shuang Jia Mi | Amitraz | Pesticide | 294.1 | 163.2 |
| 10 | Di Jun Ling | Anilazine | Pesticide | 275 | 153.1 |
| 11 | You Qu Jin | Atrazine | Pesticide | 216.1 | 174 |
| 12 | Jia Ji Gu Liu Lin | Azinphos-methyl | Pesticide | 318 | 132.2 |
| 13 | Mi Jun Zhi | Azoxystrobin | Pesticide | 404.1 | 372.1 |
| 14 | Ben Shuang Ling | Benalaxyl | Pesticide | 326 | 148.1 |

TABLE 7-continued

Summary of Detection Information for Non-quantitative Screening Drugs

| No. | Chinese Name | English Name | Drug Category | Q1 | Q3 |
|---|---|---|---|---|---|
| 15 | Bing Liu Ke Bai Wei | Benfuracarb | Pesticide | 411.2 | 195.1 |
| 16 | Bian Mi Huang Long | Bensulfuron-methyl | Pesticide | 411 | 149 |
| 17 | Ben Man Te | Benzoximate | Pesticide | 364 | 199 |
| 18 | Lian Ben Jing Zhi | Bifenazate | Pesticide | 301.1 | 170.1 |
| 19 | Lian Ben Ju Zhi | Bifenthrin | Pesticide | 440.3 | 181.1 |
| 20 | Lian Ben Sar Zuo Chun | Bitertanol | Pesticide | 338.2 | 70 |
| 21 | Ding Xian Jun An | Boscalid | Pesticide | 343 | 307 |
| 22 | Chu Cao Ding | Bromacil | Pesticide | 261 | 205 |
| 23 | Sai Qin Tong | Buprofezin | Pesticide | 306.2 | 201.1 |
| 24 | Ding Cao An | Butachlor | Pesticide | 312.1 | 238 |
| 25 | Zhong Ding Ling | Butralin | Pesticide | 296.2 | 240.1 |
| 26 | Liu Xian Lin | Cadusafos | Pesticide | 271 | 159 |
| 27 | Jia Nai Wei | Carbaryl | Pesticide | 202.1 | 145 |
| 28 | Duo Jun Ling | Carbendazim | Pesticide | 192 | 160 |
| 29 | Ke Bai Wei | Carbofuran | Pesticide | 222.1 | 165 |
| 30 | Wei Xiu Ling | Carboxin | Pesticide | 236.1 | 142.9 |
| 31 | Lv Chong Ben Jia Xian An | Chlorantra niliprole | Pesticide | 484 | 125 |
| 32 | Mie You Niao | Chlorbenzuron | Pesticide | 309 | 156 |
| 33 | Sha Chong Mi | Chlordime form | Pesticide | 197.1 | 117.1 |
| 34 | Fu Ding Niao | Chlorfluazuron | Pesticide | 540 | 158 |
| 35 | Lv Mi Huang Long | Chlorimuron-ethyl | Pesticide | 415 | 186 |
| 36 | Lv Mai Long | Chlorotoluron | Pesticide | 213.1 | 72 |
| 37 | Lv Ben An Ling | Chlorpropham | Pesticide | 214.011 | 172.1 |
| 38 | Du Si Pi | Chlorpyrifos | Pesticide | 350 | 197.9 |
| 39 | Jia Ji Du Si Pi | Chlorpyrifos-methyl | Pesticide | 321.9 | 125.1 |

TABLE 7-continued

| Summary of Detection Information for Non-quantitative Screening Drugs | | | | | |
|---|---|---|---|---|---|
| No. | Chinese Name | English Name | Drug Category | Q1 | Q3 |
| 40 | Xi Cao Tong | Clethodim | Pesticide | 360.1 | 268.2 |
| 41 | Yi E Cao Song | Clomazone | Pesticide | 240.1 | 125 |
| 42 | Sai Chong An | Clothianidin | Pesticide | 250 | 169.1 |
| 43 | Ying Du Lin | Coumaphos | Pesticide | 363 | 227 |
| 44 | Qing Shuang Zuo | Cyazofamid | Pesticide | 325 | 108.2 |
| 45 | Qing Fu Cao Zhi | Cyhalofop-butyl | Pesticide | 375.1 | 256.1 |
| 46 | Shuang Niao Qing | Cymoxanil | Pesticide | 199.1 | 128 |
| 47 | Mi Jun Huan An | Cyprodinil | Pesticide | 226.1 | 93 |
| 48 | Mie Ying An | Cyromazine | Pesticide | 167.1 | 125 |
| 49 | Nei Xi Lin | Demeton | Pesticide | 259.1 | 89 |
| 50 | Ding Mi Niao | Diafenthiuron | Pesticide | 385.1 | 329.1 |
| 51 | Er Qin Lin | Diazinon | Pesticide | 305 | 169 |
| 52 | Di Di Wei | Dichlorvos | Pesticide | 221 | 109 |
| 53 | Bai Zhi Lin | Dicrotophos | Pesticide | 238.1 | 127.1 |
| 54 | Yi Mei Wei | Diethofencarb | Pesticide | 268.1 | 226.1 |
| 55 | Ben Mi Jia Huan Zuo | Difenoconazole | Pesticide | 406.1 | 251 |
| 56 | Chu Chong Niao | Diflubenzuron | Pesticide | 311 | 158 |
| 57 | Le Guo | Dimethoate | Pesticide | 230 | 125 |
| 58 | Xi Zuo Chun | Diniconazole M | Pesticide | 326 | 70 |
| 59 | Duo Guo Ding | Dodine | Pesticide | 228.25 | 60.1 |
| 60 | Di Wen Lir | Edifenphos | Pesticide | 311 | 283 |
| 61 | Fu Huan Zuo | Epoxiconazole | Pesticide | 330 | 121 |
| 62 | Ben An Huang Long-Jia Ji | Ethametsulfuron-methyl | Pesticide | 411.1 | 196.1 |
| 63 | Yi Liu Lin | Ethion | Pesticide | 385 | 199.1 |
| 64 | Yi Chong Jing | Ethiprole | Pesticide | 397.3 | 350.9 |
| 65 | Yi Mi Fen | Ethirimol | Pesticide | 210.2 | 140.1 |
| 66 | Mie Xian Lin | Ethoprophos | Pesticide | 243 | 131 |
| 67 | Yi Yang Kui Lin | Ethoxyquin | Pesticide | 218.1 | 174 |

TABLE 7-continued

| Summary of Detection Information for Non-quantitative Screening Drugs | | | | | |
|---|---|---|---|---|---|
| No. | Chinese Name | English Name | Drug Category | Q1 | Q3 |
| 68 | Yi Man Zuo | Etoxazole | Pesticide | 360.1 | 141 |
| 69 | E Zuo Jun Tong | Famoxadone | Pesticide | 392 | 331 |
| 70 | Mi Zuo Jun Tong | Fenamidone | Pesticide | 312.1 | 92 |
| 71 | Jing Ben Zuo | Fenbuconazole | Pesticide | 337.1 | 124.9 |
| 72 | Huan Xian Jun An | Fenhexamid | Pesticide | 302 | 97 |
| 73 | Zhong Ding Wei | Fenobucarb | Pesticide | 208.1 | 95 |
| 74 | Ben Liu Wei | Fenothiocarb | Pesticide | 254.1 | 72.1 |
| 75 | Dao Wen Xian An | Fenoxanil | Pesti cide | 329.12 | 302 |
| 76 | Jing E Zuo He Cao Ling | Fenoxaprop-P-ethyl | Pesticide | 362.1 | 288.1 |
| 77 | Ding Ben Ma Lin | Fenpropimorph | Pesticide | 304.3 | 147.1 |
| 78 | Zuo Man Zhi | Fenpyroximate | Pesticide | 422 | 366.1 |
| 79 | Bei Liu Lin | Fenthion | Pesticide | 279.1 | 169 |
| 80 | Fu Ding Chong Xian An | Flonicamid | Pesticide | 230 | 203 |
| 81 | Jing Bi Fu He Cao Ling | Fluazifop-p-butyl | Pesticide | 384.1 | 282 |
| 82 | Fu Ben Chong Xian An | Flubendiamide | Pesticide | 408.1 | 274.1 |
| 83 | Fu Zuo Huang Long | Flucarbazone | Pesticide | 397.1 | 130.1 |
| 84 | Fu Chong Niao | Flufenoxuron | Pesticide | 489.1 | 158.1 |
| 85 | Zuo Mi Huang Cao An | Flumetsulam | Pesticide | 326.1 | 129.2 |
| 86 | Fu Ma Lin | Flumorph | Pesticide | 372.1 | 285 |
| 87 | Fu Cao Long | Fluometuron | Pesticide | 233.1 | 46 |
| 88 | Fu Bi Jun An | Fluopicolide | Pesticide | 382.9 | 172.9 |
| 89 | Fu Bi Jun Xian An | Fluopyram | Pesticide | 397 | 207.9 |
| 90 | Fu Gui Zuo | Flusilazole | Pesticide | 316.1 | 247.1 |
| 91 | Fu Xian An | Flutolanil | Pesticide | 324.1 | 262.1 |
| 92 | Fen Zuo Chun | Flutriafol | Pesticide | 302. 1 | 122.9 |

TABLE 7-continued

| Summary of Detection Information for Non-quantitative Screening Drugs | | | | | |
|---|---|---|---|---|---|
| No. | Chinese Name | English Name | Drug Category | Q1 | Q3 |
| 93 | Di Chong Liu Lin | Fonofos | Pesticide | 247 | 109.1 |
| 94 | Lv Bi Niao | Forchlorfenuron | Pesticide | 248.1 | 129 |
| 95 | Sai Zuo Lin | Fosthiazate | Pesticide | 284 | 104 |
| 96 | Fu Bi He Ling | Haloxyfop | Pesticide | 361.9 | 287.8 |
| 97 | Ji Zuo Chun | Hexaconazole | Pesticide | 314.1 | 70.1 |
| 98 | Huan Qin Tong | Hexazinone | Pesticide | 253.1 | 171.1 |
| 99 | Sai Man Tong | Hexythiazox | Pesticide | 353.1 | 228 |
| 100 | Yi Mei Zuo | Imazalil | Pesticide | 297.1 | 159 |
| 101 | Jia Yang Mi Cao Yan | Imazamox | Pesticide | 306.2 | 261.2 |
| 102 | Jia Mi Zuo Yan Suan | Imazapic | Pesticide | 276.1 | 163.1 |
| 103 | Mi Zuo Kui Lin Suan | Imidazoquinoic acid | Pesticide | 312.1 | 267.1 |
| 104 | Mi Zuo Yi Yan Suan | Imazethapyr | Pesticide | 290.1 | 177.1 |
| 105 | Bi Chong Lin | Imidacloprid | Pesticide | 256.1 | 175 |
| 106 | Yin Chong Wei | Indoxacarb | Pesti cide | 528.1 | 203 |
| 107 | Yi Dao Wen Jing | Iprobenfos | Pesticide | 289.1 | 91.2 |
| 108 | Lv Zuo Lin | Isazofos | Pesticide | 314 | 162 |
| 109 | Jia Ji Yi Liu Lin | Isofenphos-methyl | Pesticide | 332 | 231 |
| 110 | Yi Bing Wei | Isoprocarb | Pesticide | 211 | 95 |
| 111 | Dao Wen Ling | Isoprothiolane | Pesticide | 291.1 | 231.1 |
| 112 | Yi Bing Long | Isoproturon | Pesticide | 207.2 | 72.1 |
| 113 | Chun Lei Mei Su | Kasugamycin | Pesticide | 380.2 | 112.1 |
| 114 | Mi Jun Zhi | Kresoxim-methyl | Pesticide | 314 | 116 |
| 115 | Ru Fu He Cao Ling | Lactofen | Pesticide | 479.09 | 344 |
| 116 | Li Gu Long | Linuron | Pesticide | 249.1 | 160 |
| 117 | Ma La Liu Lin | Malathion | Pesticide | 331 | 127 |
| 118 | Shuang Que Xian Jun An | mandipropamid | Pesticide | 412.1 | 328 |

TABLE 7-continued

| Summary of Detection Information for Non-quantitative Screening Drugs | | | | | |
|---|---|---|---|---|---|
| No. | Chinese Name | English Name | Drug Category | Q1 | Q3 |
| 119 | Ben Sai Xian Cao An | Mefenacet | Pesticide | 299.1 | 148.1 |
| 120 | Mie Xiu An | Mepronil | Pesticide | 270.1 | 119 |
| 121 | Jia Ji Er Huang Long | mesosulfuron-methyl | Pesticide | 504.1 | 182 |
| 122 | Xiao Huang Cao Tong | mesotrione | Pesticide | 357 | 228.1 |
| 123 | Jia Shuang Ling | Metalaxyl | Pesti cide | 280.2 | 220 |
| 124 | Bi Cao An | Metazachlor | Pesticide | 278.2 | 134.2 |
| 125 | Jia An Lin | Methamidophos | Pesticide | 142 | 125 |
| 126 | Sha Pu Lin | Methidathion | Pesticide | 303 | 145 |
| 127 | Jia Liu Wei | Methiocarb | Pesticide | 226.1 | 121.1 |
| 128 | Mie Duo Wei | Methomyl | Pesticide | 163 | 106 |
| 129 | Jia Yang Chong Xian Jing | Methoxyfenozide | Pesticide | 369.2 | 149.1 |
| 130 | Yi Bing Jia Cao An | Metolachlor | Pesticide | 284.1 | 251.9 |
| 131 | Ben Jun Tong | Metrafenone | Pesticide | 409.3 | 209.1 |
| 132 | Qin Cao Tong | Metribuzin | Pesticide | 215.1 | 187.2 |
| 133 | Su Mie Lin | Mevinphos | Pesticide | 225 | 127 |
| 134 | He Cao Di | Molinate | Pesticide | 188.1 | 126.2 |
| 135 | Jiu Xiao Lin | Monocrotophos | Pesticide | 224.1 | 127 |
| 136 | Jing Jun Zuo | Myclobutanil | Pesticide | 289.1 | 70 |
| 137 | Di Cao An | Napropamide | Pesticide | 272.1 | 129.3 |
| 138 | Xi Ding Chong Mi | E-Nitenpyram | Pesticide | 271.2 | 126.1 |
| 139 | Da Cao Mie | Norflurazon | Pesticide | 304 | 284.1 |
| 140 | Fu Xian Niao | novaluron | Pesticide | 493 | 158.1 |
| 141 | Yang Le Guo | Omethoate | Pesticide | 214 | 109 |
| 142 | Bing Que E Cao Tong | Oxadiargyl pestanal | Pesticide | 341.1 | 151 |
| 143 | E Shuang Ling | Oxadixyl | Pesticide | 279.1 | 219.2 |
| 144 | Sha Xian Wei | Oxamyl | Pesticide | 237.1 | 72 |
| 145 | Duo Xiao Zuo | Paclobutrazol | Pesticide | 294 | 70 |
| 146 | Wu Jun Zuo | Penconazole | Pesticide | 284 | 159 |
| 147 | Er Jia Wu Ling | Pendimethalin | Pesticide | 282.1 | 212 |

TABLE 7-continued

Summary of Detection Information for Non-quantitative Screening Drugs

| No. | Chinese Name | English Name | Drug Category | Q1 | Q3 |
|---|---|---|---|---|---|
| 148 | Tian Cai Ning | phenmedipham | Pesticide | 301.1 | 136 |
| 149 | Dao Feng San | Phenthoate | Pesticide | 321 | 163.1 |
| 150 | Jia Ban Lin | Phorate | Pesticide | 261 | 75 |
| 151 | Fu Sha Liu Lin | Phosalone | Pesticide | 368 | 182 |
| 152 | Liu Huan Lin | Phosfolan | Pesticide | 256.2 | 168 |
| 153 | Ya An Liu Lin | Phosmet | Pesticide | 318 | 160 |
| 154 | Lin An | Phosphamidon | Pesticide | 300 | 174 |
| 155 | Xin Liu Lin | Phoxim | Pesticide | 299.1 | 129 |
| 156 | Zeng Xiao Mi | Piperonyl butoxide | Pesticide | 356.2 | 177.2 |
| 157 | Kang Ya Wei | Pirimicarb | Pesticide | 239.2 | 72 |
| 158 | Jia Ji Mi Ding Lin | Pirimiphos-methyl | Pesticide | 306.1 | 164.1 |
| 159 | Bing Cao An | pretilachlor | Pesticide | 312.17 | 252.12 |
| 160 | Mi Xian An | Prochloraz | Pesticide | 376.2 | 308 |
| 161 | Bing Xiu Lir | Profenofos | Pesticide | 373 | 302.9 |
| 162 | Pu Cao Jing | Prometryne | Pesticide | 242.1 | 158 |
| 163 | Du Cao An | Propachlor | Pesticide | 212.1 | 170 |
| 164 | Shuang Mei Wei | Propamocarb | Pesticide | 189 | 102 |
| 165 | Di Bai | Propanil | Pesticide | 218.1 | 127.1 |
| 166 | Ke Man Te | Propargite | Pesticide | 368 | 231 |
| 167 | Pu Mie Jin | Propazine | Pesticide | 230.1 | 146 |
| 168 | Bing Huan Zuo | Propiconazole | Pesticide | 342.1 | 159 |
| 169 | Na Cao Te | Propyzamide | Pesticide | 256 | 173.1 |
| 170 | Bing Liu Lin | Prothiofos | Pesticide | 345 | 241 |
| 171 | Bi Zuo Mi Jun Zhi | Pyraclostrobin | Pesticide | 388.1 | 194 |
| 172 | Bi Cao Mi | Pyraflufen-ethyl | Pesticide | 413 | 339 |
| 173 | Da Man Ling | Pyridaben | Pesticide | 365 | 309 |
| 174 | Mi Mei An | Pyrimethanil | Pesticide | 200 | 82 |
| 175 | Bi Bing Mi | Pyriproxyfen | Pesticide | 322.1 | 96 |
| 176 | Kui Yang Ling | Quinoxyfen | Pesticide | 308 | 162 |
| 177 | Kui He Ling | Quizalofop-ethyl | Pesticide | 373 | 299.1 |
| 178 | Yu Teng Tong | Rotenone | Pesticide | 395.1 | 213 |
| 179 | Xi He Ding | Sethoxydim | Pesticide | 328.1 | 178 |
| 180 | Xi Ma Jin | Simazine | Pesticide | 202.1 | 132.1 |
| 181 | Xi Cao Jing | Simetryn | Pesticide | 214.1 | 124.2 |
| 182 | Luo Huan Jun An | Spiroxamine | Pesticide | 298.4 | 144.2 |
| 183 | Huang Cao Tong | Sulcotrione | Pesticide | 346.02 | 139 |
| 184 | Zhi Ming Lin | Sulfotep | Pesticide | 323 | 115 |
| 185 | Wu Zuo Chun | Tebuconazole | Pesticide | 308.1 | 70 |
| 186 | Chong Xian Jing | Tebufenozide | Pesticide | 353.1 | 297.2 |

TABLE 7-continued

| Summary of Detection Information for Non-quantitative Screening Drugs | | | | | |
|---|---|---|---|---|---|
| No. | Chinese Name | English Name | Drug Category | Q1 | Q3 |
| 187 | Fu Mi Zuo | Tetraconazole | Pesticide | 372 | 159 |
| 188 | Sai Jun Ling | Thiabendazole | Pesticide | 202 | 131 |
| 189 | Sai Chong Lin | Thiacloprid | Pesticide | 253.1 | 126.1 |
| 190 | Sai Chong Qin | Thiamethoxam | Pesticide | 292 | 211 |
| 191 | Sai Ben Long | Thidiazuron | Pesticide | 221.2 | 102.1 |
| 192 | He Cao Dan | Thiobencarb | Pesticide | 258.1 | 125 |
| 193 | Liu Shuang Wei | Thiodicarb | Pesticide | 355.1 | 88.2 |
| 194 | Jia Ji Li Ku Lin | Tolclofos-methyl | Pesticide | 301 | 268.9 |
| 195 | Zuo Chong Xian An | Tolfenpyrad | Pesticide | 384.1 | 197 |
| 196 | San Zuo Tong | Triadimefon | Pesticide | 294 | 197 |
| 197 | San Zuo Chun | Triadimenol | Pesticide | 296.1 | 70.1 |
| 198 | San Zuo Lin | Triazophos | Pesticide | 314 | 119.1 |
| 199 | Ben Huang Long | Tribenuron-methyl | Pesticide | 396.1 | 155 |
| 200 | Di Bai Chong | Trichlorfon | Pesticide | 274 | 108.9 |
| 201 | San Huan Zuo | Tricyclazole | Pesticide | 190 | 163.1 |
| 202 | Wo Jun Zhi | Trifloxystrobin | Pesticide | 409 | 186 |
| 203 | Fu Jun Zuo | Triflumizole | Pesticide | 346 | 278 |
| 204 | Mie Jun Zuo | Triticonazole | Pesticide | 318 | 70 |
| 205 | Xi Xiao Zuo | Uniconazole | Pesticide | 292.1 | 70 |
| 206 | Ya Mie Duo | Vamidothion | Pesticide | 288 | 146 |
| 207 | Ben Xian Jun An | Zoxamide | Pesticide | 336 | 186.9 |
| 208 | Lv Qing Ju Zhi | Cypermethrin | Pesticide | 433 | 191 |
| 209 | Qing Wu Ju Zhi | Fenvalerate | Pesticide | 437 | 167 |
| 210 | Xiu Qing Ju Zhi | Deltamethrin | Pesticide | 523.2 | 281 |
| 211 | Fu Lv Qing Ju Zhi | Cyfluthrin | Pesticide | 451 | 191.1 |
| 212 | Lv Fu Qing Ju Zhi | Cyhalothrin | Pesticide | 450.1 | 225.1 |
| 213 | Fu Qing Wu Ju Zhi | Flucythrinate | Pesticide | 469 | 199 |
| 214 | Di Cao Kuai | Diquatdi bromide hydrate | Pesticide | 183 | 157 |
| 215 | Bai Cao Ku | Paraquat dichloride | Pesticide | 186 | 17 0.9 |
| 216 | Cao Gan Lin | Glyphosate | Pesticide | 168 | 63.1 |
| 217 | Cao An Lin | Glufosinate-ammonium | Pesticide | 180 | 63.1 |
| 218 | Xiu Dai Bi Ge Jing | Tralopyril | Pesticide | 347.1 | 79 |
| 219 | Xiu Di Ling | Bromadiolone 1 | Rodenticide | 525 | 249.9 |

TABLE 7-continued

| Summary of Detection Information for Non-quantitative Screening Drugs | | | | | |
|---|---|---|---|---|---|
| No. | Chinese Name | English Name | Drug Category | Q1 | Q3 |
| 220 | Di Shu | Diphacinone 1 | Rodenticide | 339.1 | 167.1 |
| 221 | Lv Shu Tong | Chlorophacinone 1 | Rodenticide | 372.9 | 201.1 |
| 222 | Fu Shu Ling | Flumurin 1 | Rodenticide | 541 | 160.7 |
| 223 | Sha Shu Mi | Rodenticide 1 | Rodenticide | 290.6 | 92.8 |
| 224 | Shu De Ke | difenacoum 1 | Rodenticide | 443.3 | 135 |
| 225 | Sai Shu Ling | Difethialone 1 | Rodenticide | 537 | 151 |
| 226 | Ke Shu Ling | Coumafuryl 1 | Rodenticide | 297 | 161 |
| 227 | Lv Mie Shu Ling | Coumachlor 1 | Rodenticide | 341 | 284 |
| 228 | Sha Shu Tong | Pindone 1 | Rodenticide | 229 | 116 |
| 229 | Di Shu Ling | Melitoxin 1 | Rodenticide | 335 | 161 |
| 230 | Xiu Shu Long | Brodifacoum 1 | Rodenticide | 521 | 135 |
| 231 | Fu Yi Suan | Fluoroacetic acid 1 | Rodenticide | 77 | 77 |
| 232 | Du Shu Qiang | Tetramine 1 | Rodenticide | 239 | 223 |
| 233 | Fu Yi Xian An | Fluoroacetamide | Rodenticide | 78 | 61 |
| 234 | Ben Jia Xian Ya Zi Jian | Benzolyecgonine-1 | Psychotropic drug | 290.2 | 168.3 |
| 235 | Bi Luo Xi Kang | Piroxicam-1 | Psychotropic drug | 332 | 164 |
| 236 | Ding Bing Nuo Fei | Buprenorphine-1 | Psychotropic drug | 468.2 | 396.3 |
| 237 | Dui Yi Xian An Ji Fen | 4-Acetamidophenol-1 | Psychotropic drug | 152 | 110 |
| 238 | 2-Yi Yang Ji Ben Jia Xian An | Ethenzamide | Analgesic | 166.2 | 149 |
| 239 | Luo Pai Ka Yin | Ropivacaine-1 | Psychotropic drug | 275.2 | 126.2 |
| 240 | Mei Luo Xi Kang | Meloxciam-1 | Psychotropic drug | 352 | 115 |
| 241 | Pai Ti Ding | Pethidine-1 | Psychotropic drug | 248. | 220.3 |
| 242 | Pu Lu Ka Yin | Procaine-1 | Psychotropic drug | 237.1 | 164 |
| 243 | Shu Lin Suan | Sulindac | Psychotropic drug | 357 | 233 |
| 244 | Yan Suan Qu Ma Duo | Cis-Tramadol hydrochloride-1 | Psychotropic drug | 264 | 58 |
| 245 | Qu Jia Ma Fei | Normorphine | Psychotropic drug | 272 | 272 |
| 246 | Jia Huang Suan Er Qing Mai Jiao An | Dihydroergotamine mesylate | Psychotropic drug | 584.2 | 270.2 |
| 247 | Tong Ge Suan An Ding San Chun | Ketorolac | Psychotropic drug | 256.2 | 105 |
| 248 | Tong Luo Fen | Ketoprofen | Psychotropic drug | 255 | 209 |

TABLE 7-continued

| Summary of Detection Information for Non-quantitative Screening Drugs | | | | | |
|---|---|---|---|---|---|
| No. | Chinese Name | English Name | Drug Category | Q1 | Q3 |
| 249 | Yi Ji Ma Fei | Ethylmorphine-1 | Psychotropic drug | 314.2 | 229 |
| 250 | Yi Bing An Ti Bi Lin | Isopropylantipyrine-1 | Psychotropic drug | 231.1 | 189.1 |
| 251 | You Xuan Bing Yang Fen | Dextropropoxyphene-1 | Psychotropic drug | 340 | 266 |
| 252 | Di Fen Ni Duo | Difenidol-1 | Psychotropic drug | 310.2 | 292 |
| 253 | Li Duo Ka Yin | Lidocaine-1 | Psychotropic drug | 235.2 | 86.1 |
| 254 | Luo Sha Ping | loxapine-1 | Psychotropic drug | 328.2 | 297.3 |
| 255 | Wu Fu Li Duo | Penfluridol-1 | Psychotropic drug | 524.2 | 203.2 |
| 256 | Ben Hai Suo | Trihexylphenedyl-1 | Psychotropic drug | 302.1 | 97.8 |
| 257 | Nai Pu Sheng | Naproxen-1 | Psychotropic drug | 231.2 | 185.4 |
| 258 | Ni Ke Sha Mi | N,N-DIETHYLNICOTINAMIDE-2 | Psychotropic drug | 179.3 | 108.1 |
| 259 | Yi Bing Qin | Promethazine-2 | Psychotropic drug | 285.2 | 86.1 |
| 260 | Wu Tou Jian | Aconitine | Biotoxin | 646.1 | 586.5 |
| 261 | α-Qie Jian | α-Solanine | Biotoxin | 868.6 | 398.3 |
| 262 | Ku Xing Ren Gan | Amygdalin | Biotoxin | 458.3 | 325 |
| 263 | Ye Ying Gan | PRUNASIN | Biotoxin | 296 | 163 |
| 264 | Ya Ma Qing Gan | LINUSTATIN | Biotoxin | 432.2 | 405.1 |
| 265 | Yang Di Huang Du Gan | Digitoxin | Biotoxin | 765.5 | 339.3 |
| 266 | Du Mao Xuan Hua Gan | Ouabain octahydrate | Biotoxin | 585.4 | 403.3 |
| 267 | He Tun Du Su | TETRODOTOXIN | Biotoxin | 320.1 | 302.1 |
| 268 | Ban Ao Su | Cantharidin | Biotoxin | 197.2 | 123.1 |
| 269 | α-E Gao Du Tai | BETA-AMANITIN | Biotoxin | 919.5 | 259.2 |
| 270 | E Gao Du Ying Jian | (+)-muscarine | Biotoxin | 174.1 | 57.1 |
| 271 | Huang Qu Mei Du Su B1 | Aflatoxin B1 | Biotoxin | 313.1 | 241.1 |
| 272 | Qiu Shui Xian Jian | Colchicine | Biotoxin | 400.2 | 358.2 |

Example 2. Comparison Between Different Pretreatment Methods

For TDM using a protein precipitation method, methanol/acetonitrile is most commonly used as a precipitating agent, or a mixed precipitating agent of acids or inorganic salts is added. The method is simple and efficient, but the corresponding injection solution contains a high concentration of phospholipids, which is currently regarded as a major factor affecting accuracy, precision, and instrument contamination in LC-MS detection. For pretreatment using a magnetic bead method, phospholipids of various polarities can be securely adsorbed by phospholipid depletion magnetic beads due to the application of the phospholipid depletion magnetic beads. Therefore, the content of phospholipids in the injection solution is greatly reduced, thereby reducing phospholipid interference to detection, reducing the burden on chromatographic column washing, and ensuring rapid detection.

In this example, the mixed magnetic bead method provided in Example 1 and the protein precipitation method were used respectively for sample pretreatment. A precipitating agent used in the protein precipitation method was methanol/acetonitrile (1:1), specifically, 250 μL of a methanol/acetonitrile mixed precipitating agent containing an isotope-labeled internal standard was added into 50 μL of a sample. For human serum samples 1-4, the phospholipid removal effects of the two methods were evaluated respectively. The mass spectrometry parameters and ion source parameters for detection of various phospholipids are shown in Table 8 and Table 9. The detection results are shown in Table 10.

TABLE 8

| Mass Spectrometry Parameters for Detection Using Phospholipid Depletion Magnetic Beads | | | | | | | |
|---|---|---|---|---|---|---|---|
| Lipid (Phospholipid) | Q1 Mass (Da) | Q3 Mass (Da) | Dwell (msec) | Param | DP | CE | CXP |
| LysoPC (C18:0) | 524.4 | 184.1 | 20 | DP | 30 | 30 | 14 |
| LysoPC (C16:0) | 496.1 | 184.1 | 20 | DP | 30 | 30 | 14 |
| PC (16:0/C18:2) | 758.5 | 184.1 | 20 | DP | 30 | 36 | 14 |
| PC (16:0/C18:1) | 760.5 | 184.1 | 20 | DP | 50 | 40 | 14 |
| Plasmalogen PC | 772.6 | 184.1 | 20 | DP | 30 | 30 | 14 |
| Sphingomyelin | 731.6 | 184.1 | 20 | DP | 30 | 30 | 14 |
| LysoPE (C16:0) | 454.3 | 313.3 | 20 | DP | 30 | 30 | 14 |
| PE | 768.6 | 627.5 | 20 | DP | 30 | 30 | 14 |
| LP-3 | 704 | 184 | 20 | DP | 30 | 30 | 14 |
| LP-4 | 786 | 184 | 20 | DP | 30 | 30 | 14 |

TABLE 9

| Ion Source Conditions | |
|---|---|
| Ion Source Condition | Value |
| Curtain Gas (CUR) | 25 psi |
| Ion Source Gas1 (GS1) | 55 psi |
| Ion Source Gas2 (GS2) | 55 psi |
| Ion Source Heating Temperature | 450° C. |
| Collision Gas (CAD) | 10 psi |
| IonSpray Voltage | 5500 V |

According to Table 10, it can be seen that the mixed magnetic bead method provided in Example 1 has a significantly better phospholipid removal effect than that of the protein precipitated method; after phospholipid removal, the detection results show lower phospholipid levels, indicating that a greater amount of phospholipids has been removed; moreover, the mixed magnetic bead method is simpler and more efficient in phospholipid removal and can achieve fully automated batch treatment, thereby eliminating human difference, and achieving a significant improvement effect.

TABLE 10

| Comparison of Phospholipid Removal Effects between Mixed Magnetic Bead Method and Protein Precipitation Method | | | | | | | | | | |
|---|---|---|---|---|---|---|---|---|---|---|
| Test Sample | Lyso PC (C18:0) | Lyso PC (C16:0) | PC (16:0/ C18:2) | PC (16:0/ C18:1) | Plasm alogen PC | SM | Lyso PE (C16:0) | PE | LP-3 | LP-4 |
| Magnetic bead extraction-Sample 1 | 2.89E+06 | 9.87E+05 | 6.25E+05 | 2.44E+05 | 5.31E+03 | 1.88E+04 | 2.63E+03 | 3.53E+03 | 1.79E+04 | 7.01E+04 |
| Magnetic bead extraction-Sample 2 | 3.50E+06 | 1.41E+06 | 2.45E+05 | 8.67E+04 | 1.68E+03 | 5.74E+03 | 2.60E+03 | 1.48E+03 | 7.63E+03 | 3.31E+04 |
| Magnetic bead extraction-Sample 3 | 1.59E+06 | 8.80E+05 | 5.46E+05 | 1.44E+05 | 1.86E+03 | 7.51E+03 | 4.40E+03 | 2.80E+03 | 1.05E+04 | 4.37E+04 |
| Magnetic bead extraction-Sample 4 | 1.48E+06 | 4.83E+05 | 4.74E+05 | 1.51E+05 | 2.85E+03 | 7.83E+03 | 2.97E+03 | 2.86E+03 | 8.50E+03 | 5.11E+04 |
| Protein precipitation-Sample 1 | 1.87E+07 | 2.32E+07 | 5.93E+07 | 5.82E+07 | 1.64E+06 | 7.51E+06 | 6.65E+04 | 8.10E+05 | 4.95E+06 | 1.94E+07 |
| Protein precipitation-Sample 2 | 2.31E+07 | 2.77E+07 | 6.23E+07 | 5.92E+07 | 2.40E+06 | 8.73E+06 | 6.19E+04 | 6.48E+05 | 7.46E+06 | 2.56E+07 |
| Protein precipitation-Sample 3 | 1.13E+07 | 1.92E+07 | 6.35E+07 | 6.30E+07 | 2.68E+06 | 7.19E+06 | 1.16E+05 | 1.84E+06 | 6.08E+06 | 2.17E+07 |
| Protein precipitation-Sample 4 | 1.20E+07 | 1.24E+07 | 6.50E+07 | 6.24E+07 | 2.14E+06 | 7.50E+06 | 8.84E+04 | 2.43E+06 | 5.39E+06 | 2.22E+07 |
| Phospholipid reduction ratio-Sample 1 | 84.55% | 95.75% | 98.95% | 99.58% | 99.68% | 99.75% | 96.05% | 99.56% | 99.64% | 99.64% |
| Phospholipid reduction ratio-Sample 2 | 84.85% | 94.91% | 99.61% | 99.85% | 99.93% | 99.93% | 95.80% | 99.77% | 99.90% | 99.87% |
| Phospholipid reduction ratio-Sample 3 | 85.93% | 95.42% | 99.14% | 99.77% | 99.93% | 99.90% | 96.21% | 99.85% | 99.83% | 99.80% |
| Phospholipid reduction ratio-Sample 4 | 87.67% | 96.10% | 99.27% | 99.76% | 99.87% | 99.90% | 96.64% | 99.88% | 99.84% | 99.77% |
| Average Reduction Ratio | 85.75% | 95.54% | 99.24% | 99.74% | 99.85% | 99.87% | 96.17% | 99.77% | 99.80% | 99.77% |

Example 3: Combination Effects of Different Phospholipid Depletion Magnetic Beads and Different to-be-Detected Drug-Adsorption Magnetic Beads Different phospholipid depletion magnetic beads and different to-be-detected drug-adsorption magnetic beads were combined for pretreatment for TDM, with significantly different treatment effects. In this example, different types of magnetic bead combinations shown in Table 10 were selected respectively, sample pretreatment and detection were carried out according to the method provided in Example 1, and the influences of different magnetic bead combinations on phospholipid removal effects and drug detection effects were evaluated, wherein the content of phospholipids was detected using the detection method in Example 2.

HLB magnetic extraction beads: Supplier: 3P Biosolutions; Cat. No.: MB001-1; particle size: 20-40 μm; specific surface area: about 600-750 $m^2/g$; pore size: about 80 A. MCX magnetic beads: Supplier: 3P Biosolutions; Cat. No.: MB002-1; particle size: 20-40 μm; specific surface area: about 600-750 $m^2/g$; pore size: about 80 A. MAX magnetic beads: Supplier: 3P Biosolutions; Cat. No.: MB003-1; particle size: 20-40 μm; specific surface area: about 600-750 $m^2/g$; pore size: about 80 A.

$TiO_2$ magnetic beads and $ZrO_2$ magnetic beads: customized phospholipid depletion magnetic beads; particle size: 20-40 μm, specific surface area: about 600-750 $m^2/g$; pore size: about 80 A. Their surfaces were bonded with $TiO_2$ and $ZrO_2$, respectively, as active components for phospholipid removal. The samples to be detected were serum samples. Table 11 shows the detection results for four therapeutic drugs with extraction effects being significantly affected by different magnetic bead combinations, with protein precipitation as a control.

TABLE 11

Influences of Different Magnetic Bead Combinations on Detection Results

| Phospholipid Depletion Magnetic Bead Type | To-be-detected Drug-adsorption Magnetic Bead | Residual Phospholipid Content in Supernatant (PC (16:0/C18:2) Peak Area) | Valproic Acid pKa 4.6 Peak Area | Quetiapine pKa 7.06 Peak Area | Ziprasidone pKa 9.16 Peak Area | Striripentol pKa 14.2 Peak Area |
|---|---|---|---|---|---|---|
| $TiO_2$ Magnetic Bead | HLB Magnetic Extraction Bead | 4.80E+06 | 3.78E+05 | 4.32E+06 | 3.98E+06 | 3.92E+05 |
| $ZrO_2$ Magnetic Bead | HLB Magnetic Extraction Bead | 3.30E+05 | 7.92E+05 | 7.87E+06 | 8.74E+06 | 5.24E+05 |
| N/A | HLB Magnetic Extraction Bead | 2.10E+07 | 6.78E+05 | 7.24E+06 | 7.39E+06 | 5.02E+05 |
| $TiO_2$ Magnetic Bead | MCX Magnetic Bead | 6.45E+06 | 1.35E+05 | 1.84E+06 | 1.17E+06 | 4.20E+05 |
| $ZrO_2$ Magnetic Bead | MCX Magnetic Bead | 6.89E+05 | 2.46E+05 | 2.79E+06 | 2.32E+06 | 5.38E+05 |
| N/A | MCX Magnetic Bead | 1.19E+07 | 2.19E+05 | 2.37E+05 | 2.08E+06 | 4.78E+05 |
| $TiO_2$ Magnetic Bead | MAX Magnetic Bead | 5.79E+06 | 3.56E+05 | 2.21E+06 | 1.76E+06 | 4.78E+04 |
| ZrO2 Magnetic Bead | MAX Magnetic Bead | 4.90E+05 | 6.96E+05 | 4.87E+06 | 3.74E+06 | 4.32E+04 |
| N/A | MAX Magnetic Bead | 3.49E+07 | 5.79E+05 | 4.21E+06 | 3.42E+06 | 3.98E+04 |
| Protein Precipitation Control | | 1.01E+08 | 2.74E+05 | 5.34E+06 | 4.19E+06 | 4.99E+05 |

According to Table 11, it can be seen that the use of different magnetic bead combinations results in differences in both phospholipid removal effects and drug adsorption effects. The reasons may be related to the competitive binding between magnetic bead combinations, the steric hindrance, the non-specific adsorption, and the separation efficiency. After comprehensive consideration, the optimal magnetic bead combination is a combination of HLB magnetic extraction beads and $ZrO_2$ phospholipid depletion magnetic beads, which not only maintains a good phospholipid removal effect (the lowest phospholipid content in the supernatant) and reduces a matrix effect such that the detection results are more accurate, but also increases the peak area of drugs to be detected, thereby improving detection sensitivity.

In this example, other therapeutic drugs were also validated. It is found that for each therapeutic drug, the combination of HLB magnetic extraction beads and $ZrO_2$ phospholipid depletion magnetic beads has a better phospholipid removal effect and effects of improving detection accuracy and sensitivity.

Example 4: Effect of Acid Addition

To achieve optimal extraction efficiency and better universality, when using $ZrO_2$ phospholipid depletion magnetic beads and HLB magnetic extraction beads for extraction, the acid-base properties of the solution or the proportion of the organic phase need to be strictly controlled.

In this example, pure water or water added with formic acid, citric acid, or phosphoric acid was used as a diluent. According to the method provided in Example 1, magnetic bead extraction and detection were carried out in a case where other conditions were consistent. The samples to be detected were human serum samples. The detection results are shown in Table 12. The research results prove that acid addition has a certain effect of increasing the peak area for nearly all therapeutic drugs in the samples, particularly for acidic drugs. Additionally, except for phosphoric acid, acid addition helps to improve the effect of phospholipid adsorption of the phospholipid depletion magnetic beads. However, the addition of phosphoric acid relatively reduces the effect of phospholipid adsorption of the phospholipid depletion magnetic beads because the phosphoric acid can competitively bind to the binding sites of the phospholipid depletion magnetic beads to remove the phospholipids from the phospholipid depletion magnetic beads, resulting in loose binding of the HLB magnetic extraction beads to phospholipids, thereby affecting the content of phospholipids in the final eluent. Table 12 shows the comparison between the detection results for four acidic therapeutic drugs with significant effects, with protein precipitation as a control for calculation of the increase or decrease percentage of detection results.

TABLE 12

Influences of Acid Addition to Diluents on Detection Results

| | Residual Phospholipid Content in Supernatant (PC(16:0/C18:2) Peak Area) | | Valproic Acid | | Quetiapine | | Ziprasidone | | Striripentol | |
|---|---|---|---|---|---|---|---|---|---|---|
| Sample | Peak Area | Decrease Percentage (%) | Peak Area | Increase Percentage (%) | Peak Area | Increase Percentage (%) | Peak Area | Increase Percentage (%) | Peak Area | Increase Percentage (%) |
| Protein precipitation-Serum-1 | 1.01E+08 | / | 2.74E+05 | / | 5.34E+06 | / | 4.19E+06 | / | 4.99E+05 | / |
| Protein precipitation-Serum-2 | 1.02E+08 | / | 2.72E+05 | / | 5.12E+06 | / | 4.63E+06 | / | 4.38E+05 | / |
| Magnetic beads-Dilution with water-Serum 1 | 2.37E+06 | 97.7% | 3.84E+05 | 41 | 8.58E+06 | 64 | 4.24E+06 | −4 | 4.52E+05 | −4 |
| Magnetic beads-Dilution with water-Serum 2 | 1.99E+06 | 98.1% | 4.21E+05 | 54 | 8.11E+06 | 55 | 4.45E+06 | 1 | 4.22E+05 | −10 |
| Magnetic beads-Dilution with water with 0.5% FA-Serum 1 | 4.23E+05 | 99.6% | 5.98E+05 | 119 | 8.89E+06 | 70 | 6.18E+06 | 40 | 4.82E+05 | 3 |
| Magnetic beads-Dilution with water with 0.5% FA-Serum 2 | 4.78E+05 | 99.5% | 6.04E+05 | 121 | 8.21E+06 | 57 | 6.08E+05 | 38 | 4.84E+05 | 3 |

TABLE 12-continued

Influences of Acid Addition to Diluents on Detection Results

| Sample | Residual Phospholipid Content in Supernatant (PC(16:0/C18:2) Peak Area) | | Valproic Acid | | Quetiapine | | Ziprasidone | | Striripentol | |
|---|---|---|---|---|---|---|---|---|---|---|
| | Peak Area | Decrease Percentage (%) | Peak Area | Increase Percentage (%) | Peak Area | Increase Percentage (%) | Peak Area | Increase Percentage (%) | Peak Area | Increase Percentage (%) |
| Magnetic beads-Dilution with water with 1% FA-Serum 1 | 3.30E+05 | 99.7% | 7.92E+05 | 190 | 9.87E+06 | 89 | 8.74E+06 | 98 | 5.24E+05 | 12 |
| Magnetic beads-Dilution with water with 1% FA-Serum 2 | 3.22E+05 | 99.7% | 7.45E+05 | 173 | 9.93E+06 | 90 | 8.28E+06 | 88 | 5.08E+05 | 8 |
| Magnetic beads-Dilution with water with 0.5% citric acid-Serum 1 | 9.89E+05 | 99.0% | 4.09E+05 | 50 | 8.78E+06 | 68 | 6.07E+06 | 38 | 4.46E+05 | −5 |
| Magnetic beads-Dilution with water with 0.5% citric acid-Serum 2 | 9.37E+05 | 99.1% | 3.67E+05 | 34 | 8.12E+06 | 55 | 6.32E+06 | 43 | 4.62E+05 | −1 |
| Magnetic beads-Dilution with water with 1% citric acid-Serum 1 | 6.98E+05 | 99.3% | 6.08E+05 | 123 | 9.82E+06 | 88 | 8.56E+06 | 94 | 5.18E+05 | 11 |
| Magnetic beads-Dilution with water with 1% citric acid-Serum 2 | 7.67E+05 | 99.2% | 5.97E+05 | 112 | 9.32E+06 | 78 | 8.32E+06 | 89 | 5.28E+05 | 13 |
| Magnetic beads-Dilution with water with 0.5% phosphoric acid-Serum 1 | 1.63E+07 | 84.0% | 3.36E+05 | 23 | 7.87E+06 | 50 | 5.68E+06 | 29 | 4.01E+05 | −14 |
| Magnetic beads-Dilution with water with 0.5% phosphoric acid-Serum 2 | 1.58E+07 | 84.4% | 3.67E+05 | 34 | 7.65E+06 | 46 | 5.46E+06 | 24 | 3.89E+05 | −17 |
| Magnetic beads-Dilution with water with 1% phosphoric acid-Serum 1 | 2.38E+07 | 76.6% | 4.98E+05 | 82 | 6.87E+06 | 31 | 6.32E+06 | 43 | 4.26E+05 | -9 |
| Magnetic beads-Dilution with water with 1% phosphoric acid-Serum 2 | 2.42E+07 | 76.2% | 4.69E+05 | 72 | 6.65E+06 | 27 | 6.46E+06 | 46 | 4.02E+05 | −14 |

According to Table 12, it can be seen that the acid addition to the diluent not only increases the detection peak area of therapeutic drugs but also effectively improves the phospholipid removal effect and effectively reduces the matrix content, thereby improving the accuracy of detection results. The lower the residual phospholipid content in the supernatant is, the better the effect of phospholipid adsorption of the phospholipid depletion magnetic beads is. Comparing FA and citric acid, it can be seen that the addition of formic acid more facilitates the phospholipid depletion magnetic beads in the mixed magnetic beads to exert the phospholipid removal effect.

Viewed from the detection results of valproic acid, quetiapine, ziprasidone, and stiripentol, when pure water was used as the diluent, the peak areas of valproic acid, quetiapine, ziprasidone, and stiripentol measured via magnetic bead extraction are significantly lower than those after treatment with a protein precipitation method. The reason may be that the extraction environment is inappropriate and severely affects the extraction efficiency of valproic acid, quetiapine, ziprasidone, and stevalenol. Taking valproic acid as an example, its structure includes carboxyl, with PKa of about 4.6. When pure water is used as a diluent, the pH of the solution is about 7 during magnetic bead extraction, and valproic acid exists in the solution in an ionic state, and is not easy to be fully extracted by the HLB magnetic extraction beads.

By means of the addition of 1% FA or citric acid to the diluent, the extraction rates of HLB magnetic extraction beads in the mixed extraction beads on the three drugs can be improved. The reason may be that acidic conditions can significantly suppress carboxyl ionization to maintain a neutral molecular state and can significantly improve the extraction rate of the HLB magnetic extraction beads; meanwhile, the acid-base changes can also adjust the microenvironment condition of drug-protein binding, promoting drug dissociation from proteins, thereby accelerating the extraction process of the drugs.

Meanwhile, it can also be seen that for different drugs, the addition of different acids results in that the extraction effects are not completely the same. When formic acid is added, comparing the detection results of four drugs with those after treatment with a precipitation method, all exhibit improved responses, wherein valproic acid and ziprasidone exhibit relatively more significant improvement. However, when phosphoric acid is added, the detection results of stiripentol exhibit a greater reduction compared with the addition of formic acid, and exhibit a slight reduction compared with the protein precipitation method. It is speculated that the reason for the improved response of valproic acid is the combined effects of pH and phospholipid interference. For ziprasidone, the main reason is that it has stronger protein binding (>99%) and an acidic environment is required to achieve sufficient protein dissociation. Therefore, most preferably, the addition of formic acid to the diluent can simultaneously improve the detection accuracy of the four drugs.

Example 5: Optimization of Magnetic Bead Extraction Method

In this example, during the optimization of magnetic bead extraction conditions, it was found that for most drugs, extraction is relatively rapid, and the requirements for mixing are low; however, for drugs with stronger protein binding or extremely low polarity, such as lurasidone, ziprasidone, cyclosporine, and paclitaxel, sufficient uniform mixing and shaking are required to ensure sufficient contact between magnetic beads and samples as well as complete dissociation of proteins from the samples. When different extraction conditions shown in Table 13 were applied respectively, the extraction effect of drugs with extremely low polarity such as cyclosporine and paclitaxel is directly affected, and the extraction of drugs with high protein-binding rates such as lurasidone and ziprasidone is also affected. Due to the consistent change trends of analogous drugs, only the detection results for paclitaxel and ziprasidone are shown in this example. The method provided in Example 1 was used for sample pretreatment and detection, and the influences of different extraction conditions on detection results were evaluated in a case where other conditions were consistent, as detailed in Table 13.

TABLE 13

Influences of Different Extraction Conditions on Detection of Paclitaxel and Ziprasidone

| Evaluated Extraction Conditions | Residual Phospholipid Content in Supernatant (PC(16:0/C18:2) Peak Area) | Paclitaxel: Area of substance to be detected | Paclitaxel: Extraction degree relative to 60 seconds of mixing | Ziprasidone: Area of substance to be detected | Ziprasidone: Extraction degree relative to 60 seconds of mixing |
|---|---|---|---|---|---|
| Mixing for 10 seconds + Standing for 50 seconds-Actual serum 1 | 6.98E+05 | 8.70E+04 | 73.80% | 3.81E+05 | 56.70% |
| Mixing for 10 seconds + Standing for 50 seconds-Actual serum 2 | 7.64E+05 | 8.25E+04 | | 3.64E+05 | |
| Mixing for 30 seconds + Standing for 30 seconds-1 | 7.24E+05 | 9.24E+04 | 86.30% | 5.42E+05 | 79.91% |
| Mixing for 30 seconds + Standing for 30 seconds-2 | 6.85E+05 | 1.06E+05 | | 5.08E+05 | |

TABLE 13-continued

Influences of Different Extraction Conditions on Detection of Paclitaxel and Ziprasidone

| Evaluated Extraction Conditions | Residual Phospholipid Content in Supernatant (PC(16:0/C18:2) Peak Area) | Paclitaxel Area of substance to be detected | Paclitaxel Extraction degree relative to 60 seconds of mixing | Ziprasidone Area of substance to be detected | Ziprasidone Extraction degree relative to 60 seconds of mixing |
|---|---|---|---|---|---|
| Mixing for 60 seconds-1 (Contrast Condition) | 7.08E+05 | 1.12E+05 | / | 6.38E+05 | / |
| Mixing for 60 seconds-2 (Contrast Condition) | 6.83E+05 | 1.18E+05 | | 6.76E+05 | |
| Mixing for 120 seconds-1 | 7.28E+05 | 1.00E+05 | 96.10% | 6.92E+05 | 104.64% |
| Mixing for 120 seconds-2 | 6.78E+05 | 1.21E+05 | | 6.83E+05 | |

According to Table 13, it can be seen that the optimal extraction condition is mixing for 120 seconds, which enables accurate detection without standing; the influence on the phospholipid removal effect of the phospholipid depletion magnetic beads is relatively small, and for paclitaxel and ziprasidone, the extraction effects are the best, and the detection peak areas are the highest.

Example 6: Influences of Magnetic Bead Usage Amount and Usage Method on Detection Results 1. Optimization of Magnetic Bead Usage Amount In this example, the usage amount of magnetic beads was optimized. The usage amount of magnetic beads referred to the usage amount of mixed magnetic beads (the concentration of mixed magnetic beads was 10 mg/mL, thus 0.5 mg was equivalent to 0.05 mL, 1 mg was equivalent to 0.1 mL, 2 mg was equivalent to 0.2 mL, and 3 mg was equivalent to 0.3 mL). The sample volume was 20 μL. The method provided in Example 1 was used for sample pretreatment and detection. The influences of different magnetic bead usage amounts on the detection results of therapeutic drugs were evaluated in a case where other conditions were consistent. It was found that the usage amounts most significantly affected cyclophosphamide, imatinib, and osimertinib. Since the influence on other drugs was small, only the detection results for cyclophosphamide, imatinib, and osimertinib are shown in this example, as detailed in Table 14.

TABLE 14

Influences of Magnetic Bead Usage Amount

| Testing Condition | Residual Phospholipid Content in Supernatant (PC(16:0/C18:2) Peak Area) | Cyclophosphamide Area | Imatinib Area | Osimertinib Area |
|---|---|---|---|---|
| 0.5 mg-Actual serum 1 | 6.56E+06 | 1.11E+06 | 1.21E+06 | 4.49E+05 |
| 0.5 mg-Actual serum 2 | 5.69E+06 | 1.03E+06 | 1.18E+06 | 4.33E+05 |
| 1 mg-Actual serum 1 | 7.08E+05 | 1.16E+06 | 1.56E+06 | 5.29E+05 |
| 1 mg-Actual serum 2 | 6.83E+05 | 1.22E+06 | 1.41E+06 | 5.33E+05 |
| 2 mg-Actual serum 1 | 5.23E+05 | 1.11E+06 | 1.14E+06 | 1.95E+05 |
| 2 mg-Actual serum 2 | 4.98E+05 | 1.10E+06 | 1.32E+06 | 2.00E+05 |

According to Table 14, it can be seen that some drugs are insensitive to different usage amounts of magnetic beads, with extraction rates fluctuating within a specific range, e.g., cyclophosphamide; for most drugs, as the usage amount of magnetic beads increases, the extraction rate initially rises and then slightly declines, e.g., imatinib; a very small number of drugs exhibit significantly reduced extraction rates with further increases in magnetic bead amount, e.g., osimertinib. It is speculated that the reason for the differences may be related to the binding strength between magnetic beads and drugs. For the extraction situations of all the drugs, ultimately, the magnetic bead usage amount of 1 mg (0.1 mL, 100 μL) is selected, at this point, the phospholipid removal effect is optimal, the matrix effect is the lowest, and the detection results are more accurate.

2. Use of Magnetic Bead Extraction Alone and Combined Use with Phospholipid Depletion Magnetic Beads This example further evaluated: 1. Extraction with HLB magnetic extraction beads alone; 2. Simultaneous combined use of HLB magnetic extraction beads and phospholipid depletion magnetic beads; 3. Using phospholipid depletion magnetic beads for phospholipid removal first, followed by HLB magnetic extraction beads for extraction. Comparing the extraction effects, it was found that whether to use in combination with phospholipid depletion magnetic beads had significant beneficial effects, and exhibited different influence amplitudes on detection indicators, with quetiapine, carbamazepine, and duloxetine most significantly affected. Therefore, only the detection results for quetiapine, carbamazepine, and duloxetine are shown in this example, as detailed in Table 15.

TABLE 15

Influences of Whether to Use Phospholipid Depletion Magnetic Beads

| Testing Condition | Residual Phospholipid Content in Supernatant (PC(16:0/C18:2) Peak Area) | Quetiapine RT, min | Quetiapine Area | Carbamazepine RT, min | Carbamazepine Area | Duloxetine RT, min | Duloxetine Area |
|---|---|---|---|---|---|---|---|
| Phospholipid depletion magnetic beads + HLB magnetic extraction beads-Serum 1 | 7.01E+05 | 1.83 | 1.68E+05 | 2.14 | 2.64E+06 | 2.21 | 2.25E+05 |
| Phospholipid depletion magnetic beads + HLB magnetic extraction beads-Serum 2 | 7.87E+05 | | 1.78E+05 | | 2.55E+06 | | 2.19E+05 |
| Phospholipid depletion magnetic beads + HLB magnetic extraction beads-Serum 3 | 7.42E+05 | | 1.61E+05 | | 2.63E+06 | | 2.37E+05 |
| HLB magnetic extraction beads-Serum 1 | 2.10E+07 | | 1.48E+05 | | 2.50E+06 | | 2.17E+04 |
| HLB magnetic extraction beads-Serum 2 | 2.34E+07 | | 1.51E+05 | | 2.31E+06 | | 2.10E+04 |
| HLB magnetic extraction beads-Serum 3 | 1.98E+07 | | 1.39E+05 | | 2.37E+06 | | 2.11E+04 |
| Phospholipid depletion magnetic beads first, followed by HLB magnetic extraction beads-Serum 1 | 6.90E+05 | | 4.67E+05 | | 2.54E+06 | | 2.20E+05 |
| Phospholipid depletion magnetic beads first, followed by HLB magnetic extraction beads-Serum 1 | 7.77E+05 | | 1.63E+05 | | 2.51E+03 | | 2.18E+05 |
| Phospholipid depletion magnetic beads first, followed by HLB magnetic extraction beads-Serum 1 | 7.40E+05 | | 1.57E+05 | | 2.52E+06 | | 2.25E+05 |

According to Table 15, HLB magnetic extraction beads can still achieve the extraction of the drugs to be detected without the combined use with phospholipid depletion magnetic beads. However, when the phospholipid depletion magnetic beads are not used, the residual phospholipid in the supernatant (PC(16:0/C18:2)) exhibits a peak area approximately 30 times the phospholipid response when using the phospholipid depletion magnetic beads; the response of duloxetine is strongly affected by phospholipids, and reduced by approximately 10 times when the phospholipid depletion magnetic beads are not used.

In addition, compared with the case of using phospholipid depletion magnetic beads for phospholipid removal first, followed by HLB magnetic extraction beads for extraction, it can also be found that the simultaneous combined use of HLB magnetic extraction beads and phospholipid depletion magnetic beads exhibits an improved phospholipid removal effect and a significantly better effect of extracting substances to be detected. The reason may be that when the HLB magnetic extraction beads are used in combination with the phospholipid depletion magnetic beads, the charge microenvironment of the solution is more suitable for extraction. The extraction activity of both the two types of magnetic beads on phospholipids and substances to be detected is improved, showing that the simultaneous use has a certain synergistic effect. Furthermore, simultaneous use is more convenient and simpler in operation. Therefore, the optimal method is the simultaneous combined use of HLB magnetic extraction beads and phospholipid depletion magnetic beads, not only effectively reducing the phospholipid content in the supernatant but also improving mass spectrometric response for some indicators to be detected.

In this example, other therapeutic drugs were also validated. It is found that for each therapeutic drug, the simultaneous combined use of HLB magnetic extraction beads and phospholipid depletion magnetic beads has a better phospholipid removal effect and effects of improving detection accuracy and sensitivity.

Example 7: Screening of Eluents

The eluent for mixed magnetic beads needs to meet the following conditions: 1. Being capable of efficiently eluting the drugs to be detected from HLB magnetic extraction beads; 2. Being not capable of eluting phospholipids from phospholipid depletion magnetic beads; 3. Avoiding the process of eluting the drugs to be detected from HLB magnetic extraction beads from being interfered with by the phospholipid depletion magnetic beads. In this example, the eluent formulations provided in Table 16 were used respectively, and pretreatment, elution, and drug detection were carried out according to the method provided in Example 1. It is expected to find an eluent with an optimal effect and a simplest formulation to improve the effect of TDM analysis. Since the elution effect of the eluent has different influence degrees on different drugs, lurasidone relatively significantly affected was selected as an example for illustration in this example. The detection results are shown in Table 16.

TABLE 16

| Comparison of Effects between Different Eluents | | |
|---|---|---|
| Sample | Residual Phospholipid Contentin Supernatant (PC(16:0/C18:2) Peak Area) | Lurasidone Peak Area |
| Protein precipitation-Serum-1 | 1.01E+08 | 1.02E+04 |
| Protein precipitation-Serum-2 | 1.18E+08 | 1.89E+04 |
| Protein precipitation with precipitating agent with 1% FA-Serum-1 | 1.05E+08 | 3.08E+04 |
| Protein precipitation with precipitating agent with 1% FA-Serum-2 | 9.90E+07 | 2.97E+04 |
| Magnetic bead method-Dilution with water with 1% FA-Elution with methanol-Serum 1 | 3.29E+05 | 1.91E+04 |
| Magnetic bead method-Dilution with water with 1% FA-Elution with methanol-Serum 2 | 3.31E+05 | 1.69E+04 |
| Magnetic bead method-Dilution with water with 1% FA-Elution with methanol with 0.1% FA-Serum 1 | 3.21E+05 | 4.55E+04 |
| Magnetic bead method-Dilution with water with 1% FA-Elution with methanol with 0.1% FA-Serum 2 | 3.01E+05 | 4.84E+04 |
| Magnetic bead method-Dilution with water with 1% FA-Elution with methanol with 0.1% citric acid-Serum 1 | 3.37E+05 | 2.55E+04 |
| Magnetic bead method-Dilution with water with 1% FA-Elution with methanol with 0.1% citric acid-Serum 2 | 3.04E+05 | 2.84E+04 |
| Magnetic bead method-Dilution with water with 1% FA-Elution with methanol with 0.1% phosphoric acid-Serum 1 | 3.98E+07 | 1.88E+04 |
| Magnetic bead method-Dilution with water with 1% FA-Elution with methanol with 0.1% phosphoric acid-Serum 2 | 4.32E+07 | 1.87E+04 |

The research finds that for most drugs extracted via HLB, complete elution can be achieved using pure methanol, with a very small residual amount. However, some drugs, such as lurasidone, exhibit stronger binding and require the use of acidified elution solvents for elution. Considering volatility and compatibility with subsequent detection systems, most preferably, methanol with 0.1% formic acid is used as an eluent. The use of citric acid and phosphoric acid affects the ionization efficiency during mass spectrometry detection due to their higher boiling points than formic acid. In addition, phosphoric acid can effectively elute phospholipids bound to phospholipid depletion magnetic beads, thereby affecting the phospholipid response in the supernatant.

Although the present application has been disclosed above, it is not limited thereto. Any person skilled in the art can make various changes and modifications without departing from the spirit and scope of the present application. Consequently, the scope of protection of the present application shall be defined by the scope of the claims.

The invention claimed is:

1. A method for drug detection, comprising the following steps:

making a mixed magnetic bead solution in contact with a sample, wherein the mixed magnetic bead solution comprises a magnetic bead for removing phospholipids in the sample and a magnetic bead for adsorbing a drug to be detected in the sample, such that the phospholipids and the drug to be detected in the sample are simultaneously adsorbed; and eluting, with an eluent, the drug to be detected from the magnetic bead for adsorbing the drug to be detected in the sample, and analyzing a content of the drug to be detected by liquid chromatography-tandem mass spectrometry, wherein the drug to be detected comprises any one or more of a sedative-hypnotic drug, an antidepressant drug, an antipsychotic drug, an antiepileptic drug, an antibiotic drug, an antineoplastic drug, a cardiovascular drug, and a toxicology screening drug;

wherein the magnetic bead for removing the phospholipids in the sample comprises a $ZrO_2$ silica magnetic bead, and the magnetic bead for adsorbing the drug to be detected in the sample comprises an HLB magnetic extraction bead; and wherein the mixed magnetic bead solution comprises an acid, and the acid comprises any one or more of formic acid, acetic acid, and citric acid.

2. The method according to claim 1, wherein the sedative-hypnotic drug comprises any one or more of alprazolam, clonazepam, midazolam, lorazepam, zopiclone, temazepam, bromazepam, nitrazepam, 6-hydroxybuspirone, buspirone, zaleplon, memantine, donepezil, tandospirone, diazepam, nordazepam, oxazepam, zolpidem, and estazolam;

the antidepressant drug comprises any one or more of sertraline, fluoxetine, norfluoxetine, escitalopram, fluvoxamine, paroxetine, venlafaxine, O-demethylvenlafaxine, duloxetine, mirtazapine, trazodone, milnacipran, amitriptyline, nortriptyline, doxepin, vortioxetine, norclomipramine, clomipramine, agomelatine, bupropion, mianserin, nordoxepin, and hydroxybupropion;

the antipsychotic drug comprises any one or more of olanzapine, clozapine, paliperidone, risperidone, dehydro-aripiprazole, aripiprazole, amisulpride, quetiapine, chlorpromazine, ziprasidone, norclozapine, haloperidol, perphenazine, sulpirida, norquetiapine, fluphenazine, thioridazine, atomoxetine, lurasidone, blonanserin, maprotiline, methylphenidate, rivastigmine, perospirone, norolanzapin, carbamazepine-10, 11-epoxide, norsertraline, norcitalopram, and normirtazapine;

the antiepileptic drug comprises any one or more of oxcarbazepine, lamotrigine, levetiracetam, 10-OH Car, carbamazepine, phenytoin sodium, topiramate, primidone, gabapentin, pregabalin, rufinamide, striripentol, perampanel, zonisamide, lacosamide, valproic acid, and phenobarbital;

the antibiotic drug comprises any one or more of moxifloxacin, vancomycin, tigecycline, norvancomycin, polymyxin, linezolid, ciprofloxacin, sulfamethoxazole, and levofloxacin;

the antineoplastic drug comprises any one or more of cyclophosphamide, ifosfamide, methotrexate, 5-fluorouracil, capecitabine, irinotecan, paclitaxel, docetaxel, afatinib, rivoceranib, icotinib, erlotinib, gefitinib, crizotinib, regorafenib, vemurafenib, imatinib, N-desmethylimatinib, alectinib, and osimertinib;

the cardiovascular drug comprises any one or more of metoprolol, bisoprolol, nifedipine, amlodipine, atorvastatin, ortho-hydroxyatorvastatin, rosuvastatin, losartan, losartan-metabolite, valsartan, irbesartan, telmisartan, clopidogrel-metabolite, salicylic acid, ticagrelor, and ticagrelor-metabolite M8; and the toxicology screening drug comprises any one or more of rodenticides selected from the group consisting of brodifacoum, bromadiolone, diphacinone, chlorophacinone, warfarin, flocoumafen, coumatetralyl, fluoroacetic acid, difenacoum, pindone, difethialone, coumafuryl, coumachlor, and melitoxin, pesticides, psychotropic drugs selected from the group consisting of piroxicam, 4-acetamidophenol, ethenzamide, paracetamol, sulindac, dihydroergotamine, ketorolac, ketoprofen, isopropylantipyrine, difenidol, loxapine, penfluridol, trihexylphenedyl, naproxen, N,N-diethylnicotinamide, benzoylecgonine, buprenorphine, fentanyl, flunitrazepam, ropivacaine, pethidine, procaine, oxycodone, tramadol, normorphine, ethylmorphine, dextropropoxyphene, and lidocaine, and biotoxins selected from the group consisting of aconitine, solanine, colchicine, amygdalin, ouabain octahydrate, tetrodotoxin, muscarine, and aflatoxin.

3. The method according to claim 1, wherein the eluent comprises methanol with formic acid.

4. The method according to claim 1, further providing an equilibrium solution, a diluent, and liquid chromatography mobile phase additives, wherein both the equilibrium solution and the diluent are aqueous formic acid solutions; the liquid chromatography mobile phase additives comprise an additive for mobile phase A and an additive for mobile phase B; the mobile phase A is an aqueous solution containing a mobile phase additive; the mobile phase B is a methanol solution containing a mobile phase additive; and the mobile phase additive is one or a combination of formic acid and ammonium acetate.

* * * * *